US007998672B2

(12) United States Patent
Roper

(10) Patent No.: US 7,998,672 B2
(45) Date of Patent: Aug. 16, 2011

(54) SIMULTANEOUS AMPLIFICATION AND DETECTION OF RIBONUCLEIC ACID BE AN OPTICAL METHOD USING SURFACE PLASMON RESONANCE

(75) Inventor: D. Keith Roper, Salt Lake City, UT (US)

(73) Assignee: The University of Utah Research Foundation, Salt Lake City, UT (US)

( * ) Notice: Subject to any disclaimer, the term of this patent is extended or adjusted under 35 U.S.C. 154(b) by 531 days.

(21) Appl. No.: 11/809,009

(22) Filed: May 30, 2007

(65) Prior Publication Data

US 2008/0131939 A1    Jun. 5, 2008

Related U.S. Application Data

(60) Provisional application No. 60/809,490, filed on May 30, 2006.

(51) Int. Cl.
*C12Q 1/68* (2006.01)
(52) U.S. Cl. .......................................................... 435/6
(58) Field of Classification Search ........................ None
See application file for complete search history.

(56) References Cited

U.S. PATENT DOCUMENTS

| 5,972,667 A | 10/1999 | Conia et al. |
| 2004/0086889 A1 | 5/2004 | Hwang et al. |
| 2006/0223053 A1 | 10/2006 | Roper |

FOREIGN PATENT DOCUMENTS

| WO | WO 00/55307 | 9/2000 |
| WO | WO 02/29027 | 4/2002 |
| WO | WO 02/095070 | 11/2002 |
| WO | WO 03/038127 | 5/2003 |

OTHER PUBLICATIONS

Yao et al., "Surface Plasmon field-enhanced fluorescence spectroscopy in PCT product analysis by peptide nucleic acid probes," Nucleic Acid Res., Dec. 14, 2004, vol. 32, No. 22, e177, pp. 1-6.
Li et al., "Enhancing the efficiency of a PCR using gold nanoparticles," Nucleic Acid Ress., Nov. 27, 2005, vol. 33, No. 21, e184, pp. 1-10.
International Search Report and Written Opinion from PCT/US2007/012844, Nov. 7, 2007, 10 pages.
U.S. Appl. No. 60/626,566, filed Nov. 9, 2004, Roper.
Asai, R.; Ootani, K.; Nomura, Y.; Nakamura, C.; Ikebukuro, K.; Arikawa, Y.; Miyake, J.; Karube, I. PCR-Based Ribosomal DNA Detection Technique for Microalga (*Heterosigma carterae*) Causing Red Tide and its Application to a Biosensor Using Labeled Probe. Marine Biotechnology (2003), 5(5), 417-423.
Boyer, D.; Tamarat, P.; Maali, A.; Lounis, B.; Orrit, M. Photothermal imaging of nanometer-sized metal particles among scatterers. Science (2002), 297, 1160-1163.
Caplin, B. E.; Rasmussen, R. P.; Bernard, P. S.; Wittwer, C. T. The most direct way to monitor PCR amplification for quantification and mutation detection. Biochemica (1999), 1, 5-8.

Carslaw H. S.; Jaeger, J. C. Conduction of Heat in Solids. 2.sup.nd Ed. Clarendon Press: Oxford. 1959 Cooper, F. Int J Heat Mass Transfer (1977) 991.
Demers, L. M; Oestblom, M; Zhang, H.; Jang, N.-H.; Liedberg, B.; Mirkin, C. A. Thermal Desorption Behavior and Binding Properties of DNA Bases and Nucleosides on Gold. Journal of the American Chemical Society (2002), 124(38), 11248-11249.
Duff, D. G.; Baiker, A.; Edwards, P. P. A new hydrosol of gold clusters. 1. Formation and particle size variation. Langmuir (1993), 9(9), 2301-9.
Feriotto, G.; Gambari, R. Surface plasmon resonance based biosensor technology for real-time detection of PCR products. PCR Technology (2nd Edition) (2004), 141-153.
Goodrich, T. T.; Lee, H. J.; Corn, R. M. Direct Detection of Genomic DNA by Enzymatically Amplified SPR Imaging Measurements of RNA Microarrays. Journal of the American Chemical Society (2004), 126(13), 4086-4087.
Halte, V.; Bigot, J.-Y.; Palpant, B.; Broyer, M.; Prevel, B.; Perez, A. Size dependence of the energy relaxation in silver nanoparticles embedded in dielectric matrices. Applied Physics Letters (1999), 75(24), 3799-3801.
Hamad-Schifferil, K.; Schwartz, J. J.; Santos, A. T.; Zhang, S.; Jacobson, J. M. Remote electronic control of DNA hybridization through inductive coupling to an attached metal nanocrystal antenna. Nature (London, United Kingdom) (2002), 415(6868), 152-155.
Hartland, Gregory V. Coherent vibrational motion in metal particles: Determination of the vibrational amplitude and excitation mechanism. Journal of Chemical Physics (2002), 116(18), 8048-8055.
He, L.; Musick, M. D.; Nicewamer, S. R.; Salinas, F. G.; Benkovic, S. J.; Natan, M.J.; Keating, C. D. Colloidal Au-enhanced surface plasmon resonance for ultrasensitive detection of DNA hybridization. Journal of the American Chemical Society (2000), 122(38), 9071-9077.
Hu, M.; Hartland, G. V. Heat Dissipation for Au Particles in Aqueous Solution: Relaxation Time versus Size. Journal of Physical Chemistry B (2002), 106(28), 7029-7033.
Hu, M.; Hartland, G. V. Heat Dissipation for Au Particles in Aqueous Solution: Relaxation Time versus Size [Erratum for 2002, vol. 106B]. Journal of Physical Chemistry B (2003), 107(5), 1284.
Hu, M.; Wang, X.; Hartland, G. V.; Salgueirino-Maceira, Veronica; Liz-Marzan, Luis M. Heat dissipation in gold-silica core-shell nanoparticles. Chemical Physics Letters (2003), 372(5,6), 767-772.
Huettmann, G.; Radt, B.; Serbin, J.; Birngruber, R. Inactivation of proteins by irradiation of gold nanoparticles with nano- and picosecond laser pulses. Proceedings of SPIE—The International Society for Optical Engineering (2003), 5142 (Therapeutic Laser Applications and Laser-Tissue Interactions), 88-95.
Iborra, F. J.; Pombo, A.; McManus, J.; Jackson, D. A.; Cook, P. R. The topology of transcription by immobilized polymerases. Experimental Cell Research (1996), 229(2), 167-173.
Incropera, F. P.; DeWitt, D. P. Fundamentals of Heat and Mass Transfer. 2.sup.nd Ed. John Wiley & Sons: New York. 1985.

(Continued)

*Primary Examiner* — Heather Calamita
(74) *Attorney, Agent, or Firm* — Workman Nydegger

(57) ABSTRACT

Methods of performing PCR are provided. Methods may include using an optical source to provide heating for thermocyling the PCR reaction. Methods may include using surface plasmon resonance and/or fluorescence resonance enhanced transfer to allow real-time monitoring of a PCR reaction. Methods may include immobilizing a template, primer, or polymerase on a surface such as a gold or other surface plasmon resonance active surface.

22 Claims, 9 Drawing Sheets

OTHER PUBLICATIONS

Jin R.; Wu G.; Li Z.; Mirkin C. A.; Schatz G. C. What Controls the Melting Properties of DNA-Linked Gold Nanoparticle Assemblies? J. Am. Chem. Soc. (2003) 125:1643-1654.

Kai, E.; Sawata, S.; Ikebukuro, K.; Iida, T.; Honda, T.; Karube, I. Detection of PCR products in solution using surface plasmon resonance. Analytical Chemistry (1999), 71(4), 796-800.

Kornberg, A.; Baker, T. A. DNA Replication 2.sup.nd Ed. W.H. Freeman & Co: New York 1991.

Lindroos, K.; Liljedahl, U.; Raitio, M.; Syvanen, A.-C. Minisequencing on oligonucleotide microarrays: comparison of immobilization chemistries. Nucleic Acids Research (2001), 29(13), e69/1-e69/9.

Link, S.; El-Sayed, M. A. Optical properties and ultrafast dynamics of metallic nanocrystals. Annual Review of Physical Chemistry (2003), 54 331-366.

Molecular Biology of the Cell@NCBI, Accessed May, 2004. (http://www.ncbi.nlm.nih.gov/books/bv.fcgi?tool=bookshelf&call=bv.View.ShowSection&searchterm=human&rid=cell.section.1607#1608).

Myszka, D. G.; He, X.; Dembo, M.; Morton, T. A.; Goldstein, B. Extending the range of rate constants available from BIACORE: interpreting mass transport-influenced binding data. Biophysical Journal (1998), 75(2), 583-594.

Nilsson, J.; Bosnes, M.; Larsen, F.; Nygren, P.-A.; Uhlen, M.; Lundeberg, J. Heat-mediated activation of affinity-immobilized Taq DNA polymerase. BioTechniques (1997), 22(4), 744-746, 748-751.

Oldenburg, S.J.; Jackson, J.B.; Westcott, S.L.; Halas, N.J. Infrared extinction properties of gold nanoshells. Applied Physics Letters (1999), 75(19), 2897-2899.

Park, S-J.; Taton, T. A.; Mirkin, C. A. Array-based electrical detection of DNA with nanoparticle probes. Science (2002), 295(5559), 1503-1506.

Pastinen, T.; Kurg, A.; Metspalu, A.; Peltonen, L.; Syvanen, A.-C. Minisequencing: a specific tool DNA analysis and diagnostics on oligonucleotide arrays. Genome Research (1997), 7(6), 606-614.

Power, G. M.; Barrett, D. A.; Davies, M. C.; Pitfield, I. D.; Shaw, P. N. The study of BSA adsorption onto model-reversed phase chromatography surfaces using surface plasmon resonance. Book of Abstracts, 216th ACS National Meeting, Boston, Aug. 23-27, 1998.

Radt, B.; Serbin, J.; Lange, B. I.; Birngruber, R.; Huettmann, G. Laser-generated micro- and nanoeffects: inactivation of proteins coupled to gold nanoparticles with nano- and picosecond pulses. Proceedings of SPIE—The International Society for Optical Engineering (2001), 4433(Laser-Tissue Interactions, Therapeutic Applications, and Photodynamic Therapy), 16-24.

Roper, D. K. Enhancing Lateral mass transport to Improve the Dynamic Range of Adsorption Rates Measured by Surface Plasmon Resonance. Chem. Eng. Sci. (2006), 61(8), 2557-2564.

Roper, D. K. 2004b. Enhancing Lateral Mass Transport to Improve the Dynamic Range of Surface Plasmon Resonance and to Measure Macromolecule Adsorption Directly on 3-D Surfaces. Biophysical Journal. Submitted.

Roper, D. K. 2004c. Adenovirus Binding Measured by Surface Plasmon Resonance. AIChE Annual Meeting, Austin Tex. Nov. 8-12.

Roper, D. K.; Johnson, A; Lee, A; Taylor, J; Trimor, C; Wen, E. Membrane Filtration in Vaccine Bioprocessing. First International Conference on Membrane and Filtration Technology in Biopurification, Cambridge, U.K. Apr. 7-9, 1999.

Roper, D.K.; Lightfoot, E.N. Estimating Plate Heights in Stacked-Membrane Chromatography by Flow-Reversal. J. Chromatogr. A. 702(1-2) (1995) 69-80.

Roper, D. K., Nakra, S. Adenovirus Type 5 Intrinsic Adsorption Rates, 2006.

Measured by Surface Plasmon Resonance. Anal. Biochem. (2006), 348, 75-83.

Roper, D. K.; Nakra, S. Surface Plasmon Resonance of Adenovirus Type 5 Binding to Diethylaminoethyl-Derivatized Self Assembled Monolayers. Analytical Chemistry. Submitted 2004.

Roper, D. K.; Purdom, G. Adenovirus Binding, Elution and Equilibrium Measured by Surface Plasmon Resonance. PREP 2004, Baltimore, Md. May 24-26, 2004.

Schultz, D. A. Plasmon Resonant Particles for Biological Detection. Curr Opin Biotechnol. 2003 14:13-22.

Storhoff, J. J.; Elghanian, R.; Mirkin, C. A.; Letsinger, R. L. Sequence-Dependent Stability of DNA-Modified Gold Nanoparticles. Langmuir (2002), 18(17), 6666-6670.

Svitel, J.; Balbo, A.; Mariuzza, R. A.; Gonzales, N. R.; Schuck, P. Combined affinity and rate constant distribtions of ligand populations from experimental surface binding kinetics and equilibria. Biophysical Journal (2003), 84(6), 4062-4077.

Talmaci R; Traeger-Synodinos J; Kanavakis E; Coriu D; Colita D; Gavrila L. Scanning of beta-globin gene for identification of beta-thalassemia mutation in Romanian population. Journal of cellular and molecular medicine (Apr.-Jun. 2004), 8(2),232-40.

Taton, T. A.; Mirkin, C. A.; Letsinger, R. L. 2000. Science 298:1757.

Tsoi, P.Y.; Yang, J.; Sun, Y.; Sui, S.; Yang, M. Surface Plasmon Resonance Study of DNA Polymerases Binding to Template/Primer DNA Duplexes Immobilized on Supported Lipid Monolayers. Langmuir (2000), 16(16), 6590-6596.

Vet, J. A. M.; Marras, S. A. E. Design and optimization of molecular beacon real-time polymerase chain reaction assays. Methods in Molecular Biology (Totowa, N.J., United States) (2005), 288(Oligonucleotide Synthesis), 273-290.

Wang, Y.; Prosen, D. E.; Mei, L.; Sullivan, J. C.; Finney, M.; Vander Horn, P. B. A novel strategy to engineer DNA polymerases for enhanced processivity and improved performance in vitro. Nucleic Acids Research (2004), 32(3), 1197-1207.

Westcott, S. L.; Averitt, R. D.; Wolfgang, J. A.; Nordlander, P.; Halas, N. J. Adsorbate-Induced Quenching of Hot Electrons in Gold Core-Shell Nanoparticles. Journal of Physical Chemistry B (2001), 105(41), 9913-9917.

Wilson, O. M.; Hu, X.; Cahill, D. G.; Braun, P. V. Colloidal metal particles as probes of nanoscale thermal transport in fluids. Physical Review B: Condensed Matter and Materials Physics (2002), 66(22), 224301/1-224301/6.

Wittwer, C. T.; Herrmann, M. G.; Moss, A. A.; Rasmussen, R. P. Continuous fluorescence monitoring of rapid cycle DNA amplification. BioTechniques (1997), 22(1), 130-131, 134-138.

Yao D: "PCR products analysis by surface Plasmon-based biosensors", Dissertation, May 2004, pp. 1-111 XP002613470 Mainz, DE Retrieved from the Internet: URL: http://www.pmip-mainz.mpg.de/knoll/publications/thesis/yao_2004.pdf.

Theil A J et al: "In Situ Surface Plasmon Resonance Imaging Detection of DNA Hybridization to Oligonucleotide Arrays on Gold Surfaces", Analytical Chemistry, American Chemical Society, US, vol. 69, No. 24, Dec. 15, 1997, pp. 4948-4956, XP000733394, ISSN: 0003-2700, DOI: 10.1021/AC9708011.

Krone J R et al: "BIA/MS: Interfacing biomolecular interaction analysis with mass spectrometry" Analytical Biochemisty, Academic Press Inc, New York vol. 244, Jan. 1, 1997 pp. 124-132 XP002978973, ISSN: 0003-2697, DOI: 10.1006/ABIO.1996.9871.

Garwe F et al: "Laser pulse energy conversion on sequence specifically bound metal nanoparticles and its application for DNA manipulation", Medical Laser Application, Elsevier, NL, vol. 20, No. 3, Oct. 14, 2005, pp. 201-206 XP025339423, ISSN: 1615-1615, DOI: 10.1016/J.MLA.2005.07.007.

Supplemental International Search Report and Written Opinion cited in European Application No. 07795546.6, mailed Dec. 27, 2010.

SEQUENCE LISTING

<160> NUMBER OF SEQ ID NOS: 4

<210> SEQ ID NO 1
<211> LENGTH: 20
<212> TYPE: DNA
<213> ORGANISM: Artificial
<220> FEATURE:
<223> OTHER INFORMATION: PCR primer

<400> SEQUENCE: 1
acacaactgt gttcactagc                                             20

-continued

```
<210> SEQ ID NO 2
<211> LENGTH: 20
<212> TYPE: DNA
<213> ORGANISM: Artificial
<220> FEATURE:
<223> OTHER INFORMATION: PCR primer

<400> SEQUENCE: 2
caacttcatc cacgttcacc                                              20

<210> SEQ ID NO 3
<211> LENGTH: 20
<212> TYPE: DNA
<213> ORGANISM: Artificial
<220> FEATURE:
<223> OTHER INFORMATION: PCR primer

<400> SEQUENCE: 3
gctcactcag tgtggcaaag                                              20

<210> SEQ ID NO 4
<211> LENGTH: 22
<212> TYPE: DNA
<213> ORGANISM: Artificial
<220> FEATURE:
<223> OTHER INFORMATION: PCR primer

<400> SEQUENCE: 4
ggttggccaa tctactccca gg                                           22
```

SIMULTANEOUS AMPLIFICATION AND DETECTION OF RIBONUCLEIC ACID BE AN OPTICAL METHOD USING SURFACE PLASMON RESONANCE

CROSS-REFERENCE TO RELATED APPLICATIONS

Under the provisions of 35 U.S.C. §119(e), priority is claimed from U.S. Provisional Application Ser. No. 60/809,490 filed May 30, 2006, the contents of which are incorporated herein by this reference.

TECHNICAL FIELD

The invention relates to the field of nano/biotechnology, and gene sequencing nucleic acid analysis. Specifically, the invention relates to simultaneous amplification and real-time detection of a nucleic acid template by polymerase chain reaction (PCR) using surface-plasmon-resonance.

BACKGROUND OF THE INVENTION

Analysis of an estimated 5000 genetic disorders linked to hereditary disease and identification of ~1.4 million single nucleotide polymorphisms (SNP) rely on gene amplification by PCR. Mutations in the β-globin gene, for example, result in sickle cell anemia and β-thalassaemia, with symptoms ranging from mild to severe anemia (Talmaci et al., 2004). Cancer, diabetes, hemophilia, cystic fibrosis, heart disease, musculoskeletal disorders and many other diseases can have a genetic basis. Increasing the speed and sensitivity of PCR could improve diagnosis of genetic diseases and enhance the development of therapeutic or prophylactic countermeasures.

SPR Detection of DNA: Label-free biomolecular interaction analysis (BIA) of DNA (Feriotto & Gambari, 2004; Goodrich et al., 2004) including PCR products (Kaie et al., 1999) has been evaluated in planar SPR sensors like commercially-available BIACore™ (BIACore) or Spreeta™ (Texas Instruments) analyzers. Single-base pair mismatches at or near the 3' end of template/primer dsDNA could be distinguished by SPR based on relative binding efficiencies to DNA polymerase I (Tsoi et al., 2000). Sequencing of polynucleotides by interaction with immobilized DNA polymerase and SPR-based detection of ensuing effects has been suggested (Densham, 2002). These studies show DNA detection by SPR can reach 1-500 femtomolar levels (Goodrich et al., 2004; Park et al., 2002) with point mutation selectivity factors of ~$10^5$:1 (Park et al., 2002), although simultaneous laser-induced amplification and real-time detection of template DNA have not been reported.

Extinction properties of plasmon resonant nanoparticles (NP) have been examined (Oldenburg et al., 1999; Westcott et al., 2001) and have been applied to detect bound DNA (Park et al., 2002; Schultz, 2003; Storhoff et al., 2002; Taton et al., 2000). These reports have not examined solid-phase amplification by polymerase or primers bound to planar- or nanoparticle-Au surfaces, but they show how ionic strength and chain length affect Au-oligonucleotide interactions including aggregation, binding, hybridization and denaturation.

Immobilizing Primers and Probes on Au Surfaces: Minisequencing on oligonucleotide microarrays is promising for large-scale DNA analysis and detection of single nucleotide polymorphisms (SNP) (Lindroos et al., 2001; Pastinen et al., 1997). Real-time SPR-induced minisequencing using primers or probes on Au surfaces has not been reported, although DNA has been immobilized on NP and hybridized NP-DNA conjugates have been detected by SPR. Storhoff et al. (2002) showed linking alkanethiol-capped poly-T, C or A to Au NPs prevented aggregation in $\leq$1M NaCl using 8- and 12-np oligos, and in 0.07-1.2M $MgCl_2$ using larger oligos in the range 5- to 15-bp. Cleaving 5' disulfide bonds of alkanethiol-capped oligonucleotides permitted Au-thiol covalent bond formation and gave surface coverages of ~$10^{13}$ strands/$cm^2$ (Jin et al., 2003). This yielded ~90, 160 and 250 single strands per 13, 31 and 50-nm NP, respectively. Alkanethiol-capped poly-T gave higher Au surface coverages than poly-C or -A, preventing non-specific Au-DNA interactions from amine or carbonyl functional groups and backbone phosphate groups and providing greater stability (Demers et al., 2002). Cyclic dithiane-epiandrosterone disulfide linkers and trithiol-capped oligonucleotides increased stability of DNA-oligo covalent bonds in the presence of dithiothreitol, which is present as a stabilizer in some PCR buffers (Shultz, 2003).

Probe Hybridization, Primer Annealing and Denaturation on Au Surfaces: Au-NP-immobilized alkanethiol-capped oligos that were hybridized to complementary oligos exhibited sharp melting profiles and higher melt temperatures ($T_m$) than analogous oligos with molecular fluorophore probes (Storhoff et al., 2002). This effect arose from multiple links between NP and local ionic strength effects. Melt-curve sharpness and $T_m$ increased with immobilized probe density, with poly-A spacer length from 0 to 30 bp, and with NP size from 13 to 50 nm at constant concentrations of NP and target (Jin et al., 2003). Melting temperatures increased from 41 to 61.5° C. and hybridization rates increased as NaCl content increased from 0.05 to 1.0 M. Hybridization with immobilized oligos was not detected for NaCl<0.05 M at room temperature. Changing NaCl content ~0.1M induced melting or denaturation at $T<T_m$.

Immobilizing Polymerase on Au Surfaces: Research on chromatin loops suggests template slides past DNA and RNA polymerases immobilized in vivo in large transcription factories (Iborra et al., 1996). DNA polymerase covalently linked to a surface via amide-bond formation retained 10% of its solution-phase activity when its active site was masked by substrate during immobilization (Hwang et al., 2002; Hwang et al., 2004). In contrast, Taq DNA polymerase fused to a human serum albumin (HSA) binding protein yielded little extension product after affinity-immobilization to a HSA-coated surface (Nilsson et al., 1997). Transcriptional fidelity, reliability and yield is increased by covalently linking the polymerase domain to a sequence non-specific DNA binding protein to impart a sliding grip on the minor groove (Pelletier, 2000; Wang et al., 2004). This enhanced polymerase processivity 2-fold relative to Taq and 12-fold relative to other high-fidelity polymerases, yielding a transcription rate of 3.8 kilobasepairs (kb) per minute. This rate correlates well with replication-fork movement of 0.5 to 5 kb per minute in eukaryotic chromosomes, but is well below prokaryotic rates of almost 100 kb per minute (Kornberg & Baker, 1992). Immobilizing polymerase to perform PCR amplification could be readily integrated into Lab-on-a-Chip devices (Hwang et al., 2003).

SPR-Induced Heating of Au Surfaces: Titanium:sapphire (Ti:sapphire) laser pumping is the method most frequently used to dissipate heat from Ag and Au nanoparticles (Boyer et al., 2002; Halte, et al., 1999; Hu & Hartland, 2002) and Au—Si nanoshells (Hu et al, 2003) and to inactivate Au-surface-associated proteins (Huettmann, et al., 2003; Radt et al, 2001). However, heating for thermal melting, binding, or desorption of DNA bases and nucleotides interacting with Au surfaces has been induced only by changing bulk solution temperature (Demers et al., 2002; Jin et al., 2003) or by inductive coupling (Hamad-Schifferil et al., 2002). Inductive coupling of radio-frequency magnetic field to 1.4-nm Au nocrystals with a power output of 1-4 watts increased apparent temperature 13° C., but this increase is insufficient for PCR thermal cycling.

Femtosecond laser pulses excite nonlocalized Au electrons to create a highly nonisothermal electron distribution that relaxes within 500 fs by electron-electron scattering to establish a new distribution corresponding to a higher temperature (Link & El-Sayed, 2003). Temperature (T) increased in NP with diameters from 5 to 50 nm in proportion to pump laser flux (intensity, $I_o$/spot size, σ), a function of sample absorbance (A), and the inverse of sample heat capacity, $C_p$, Au concentration, and cell pathlength (l), respectively, according to Beers Law:

$$\Delta T = \frac{I_o(1-\zeta)^2(1-10^{-A})}{\sigma[Au]C_p l} \quad (1)$$

In Eq 1, $(1-\zeta)^2$ with $\zeta \sim 0.04$ accounts for pump laser scattering in the sample cell. Temperature increases (ΔT) of 40 K were produced in 15 nm Au NP using 0.2 μJ/pulse/6×10$^{-4}$ cm$^2$ pump power from a regeneratively amplified Ti:sapphire laser (λ=780 nm; 0.5 mJ/pulse/; 120 fs fwhm sech$^2$ deconvolution; 1 kHz repetition rate) (Hu and Hartland, 2002). Much higher laser fluxes were required to inactivate Au-NP-bound proteins. Thirty-five ps pulses at 527 nm with 50 mJ/cm2, and 16 ns pulses at 450 mJ/cm2 inactivated 80% and 100% of alkaline phosphatase bound to 15-nm NP, respectively (Radt et al, 2001). These studies did not report rapid cycling of SPR-induced thermal dissipation to anneal, elongate or denature DNA strands but they are useful to design conditions for SPR-based PCR. Ti:sapphire laser pumping, continuous Argon-ion lasing, or alternate optical sources that stimulate surface plasmon resonance can achieve ΔT=17 K and ΔT=39 K required for elongation and denaturation, respectively, relative to an ambient temperature of 55° C. without inactivating Taq or Phusion™ polymerase.

Characteristic Time Scale for Temperature Dissipation: Gold electrons excited by femtosecond laser light exchange energy with the environment via pump-power dependent electron-phonon coupling (Link & El-Sayed, 2003). Particle temperatures in aqueous Au sols dissipate with time, T(t), relative to the surrounding ($T_s$) and initial ($T_i$) temperatures, according to a phenomenological stretched exponential function (Hu & Hartland, 2002):

$$\frac{T(t)-T_s}{T_i-T_s} = \exp\{-(t/\tau)^\beta\} \quad (2)$$

where τ=0.64 picoseconds nm$^{-2}$×R$^2$ for R in nm, and β=0.6 and 0.7 for 2R=5 nm to 15 nm and 26 nm to 50 nm particles, respectively. Observed characteristic decay times increased from 10 ps for 2R=5-nm Au NP to 380 ps for 2R=50-nm Au NP. The energy-dissipation time-scale, $\tau_d$, may be estimated in general (Wilson et al, 2002) by equating the heat capacity of radius R particles, $4/3\pi R^3 C_p$, to the heat capacity of adjoining thermal diffusion layer of thickness $l_d=(\alpha\tau_d)^{1/2}$, where α is thermal diffusivity. The heat capacity of the diffusion layer is $4\pi R^2 l_d C_f$. The time scale is then:

$$\tau_d = \frac{r^2 C_p^2 \rho_f}{9 C_f k_f} \quad (3)$$

Eq. 3 shows $\tau_d$ increases proportional to particle surface area for 2R=5 nm or larger and inversely with thermal conductivity, $k_f$, and heat capacity, $C_f$, of surrounding medium, which is consistent with an absence of interface effects. Immobilizing alkanethiol-capped DNA onto Au NP changes the interface thermal conductance, G, which has units of Wm$^{-2}$K$^{-1}$, and delays energy exchange between surface Au atoms and surrounding molecules. The characteristic decay may then be estimated as (Wilson et al, 2002):

$$\tau_i = \frac{rC_p}{3G} \quad (4)$$

Although G>20 MW m$^{-2}$K$^{-1}$ was reported for dodecanethiol-terminated 2R=3-5 nm Au NP, a potential electron effect at the Au-alkanethiol interface increased the observed decay about 10-fold relative to the value obtained with Eq 4. Amplification of 110- and 536-bp fragments of human β-globin gene would take about 66 and 330 milliseconds, respectively at a rate of 1667 bp per sec (Kornberg & Baker, 1991).

Characteristic Length Scale for Temperature Dissipation: Using a $A_{20}$ spacer (Jin et al., 2003) between the forward/reverse primer pairs and the Au surface gives total lengths (fragment plus spacer) of 44 and 189 nm for 110- and 536-bp fragments of human β-globin, respectively, since 106 nucleotides occupy a linear distance of 3.4×10$^5$ nm (Molecular Biology at NCBI, 2004).

Commercially-Available Thermal Cyclers vs. Real-Time PCR: PCR steps in conventional block thermal cyclers take 20 to 60 seconds each. Hours are required for 35-45 cycles to achieve end-point gene levels that are detectable by subsequent ethidium bromide or fluorescent staining of gels. Real-time PCR methods that quantify genes with fluorescent labels are more reproducible, have a wider dynamic range and eliminate risk of carryover contamination (Vet & Marras, 2005). Real-time fluorescent-label methods avoid second round amplification, false positives, or confirmational sequencing. Fluorescent SYBR green dye intercalates dsDNA during annealing and extension steps, but melt temperatures, $T_m$, must be analyzed to distinguish signal from SYBR interaction with desired amplicons from non-specific interaction with primer dimers. Using FRET from donor 3'-fluorescein to adjacent acceptor cyanine dye Cy5 or 5'-LC Red 640 labeled on amplicon-specific hybridization probes that are 23-35 bp long reduces non-specific background signal (Wittwer et al., 1997). LightCycling™, the fastest real-time PCR method, heats template samples in glass capillaries by forced air and continuously monitors DNA formation by fluorescence. LightCycling™ can detect ~100 initial copies and finish in 10 to 15 minutes.

SPR decreases the intensity of light reflected at a specific angle from a conducting gold film adjacent to a dielectric medium (glass and sample). The setup for SPR with planar- or NP-Au surfaces is shown in FIG. 1. At the angle of minimum reflectance, incident light photons excite delocalized metal electrons, causing them to oscillate collectively and dissipate light energy. The minimum angle varies with the sample refractive index close to the glass surface. β-globin template that binds to immobilized forward/reverse primers increases the local refractive index (RI), shifting the angle of minimum reflectance in proportion to mass concentration, producing a SPR sensorgram. RI changes are detectable within ~200 nm of flat Au surfaces and within 10 to 20 nm of 40-nm Au NP

BRIEF SUMMARY OF THE INVENTION

A method of simultaneous amplification of nucleic acid (e.g., DNA) by optically-induced thermal cycling, coupled with real time detection of PCR amplicons by SPR is described. In one aspect, the method comprises immobilizing a polymerase or forward/reverse primers on a gold surface, inducing heating and/or thermal cycling by optical stimulation of surface plasmon resonance resulting in rapid thermal dissipation, and measuring rates and magnitudes of interaction between the template and molecules immobilized on the gold surface by analyzing mass-induced changes at resonance absorption with SPR.

In one embodiment, amplification efficiencies are measured using fluorescence resonance enhanced transfer from a donor 3'-flourescein to acceptor 5'-LC red 5640 on adjacent hybridization (polynucleotide) probes.

In one embodiment, immobilization of molecules on the gold surface may be catalyzed using N-hydrosuccininmide, N'(ethylcarbonimidoyl)-N,N-dimethylpropatne-1,3-diamine hydrochloride, or diethylehtylenediamine covalently bonded to alkanethiol groups on the gold In a further embodiment, temperature cycling may be performed with a Ti:sapphire laser.

DETAILED DESCRIPTION OF THE INVENTION

Figure 1:
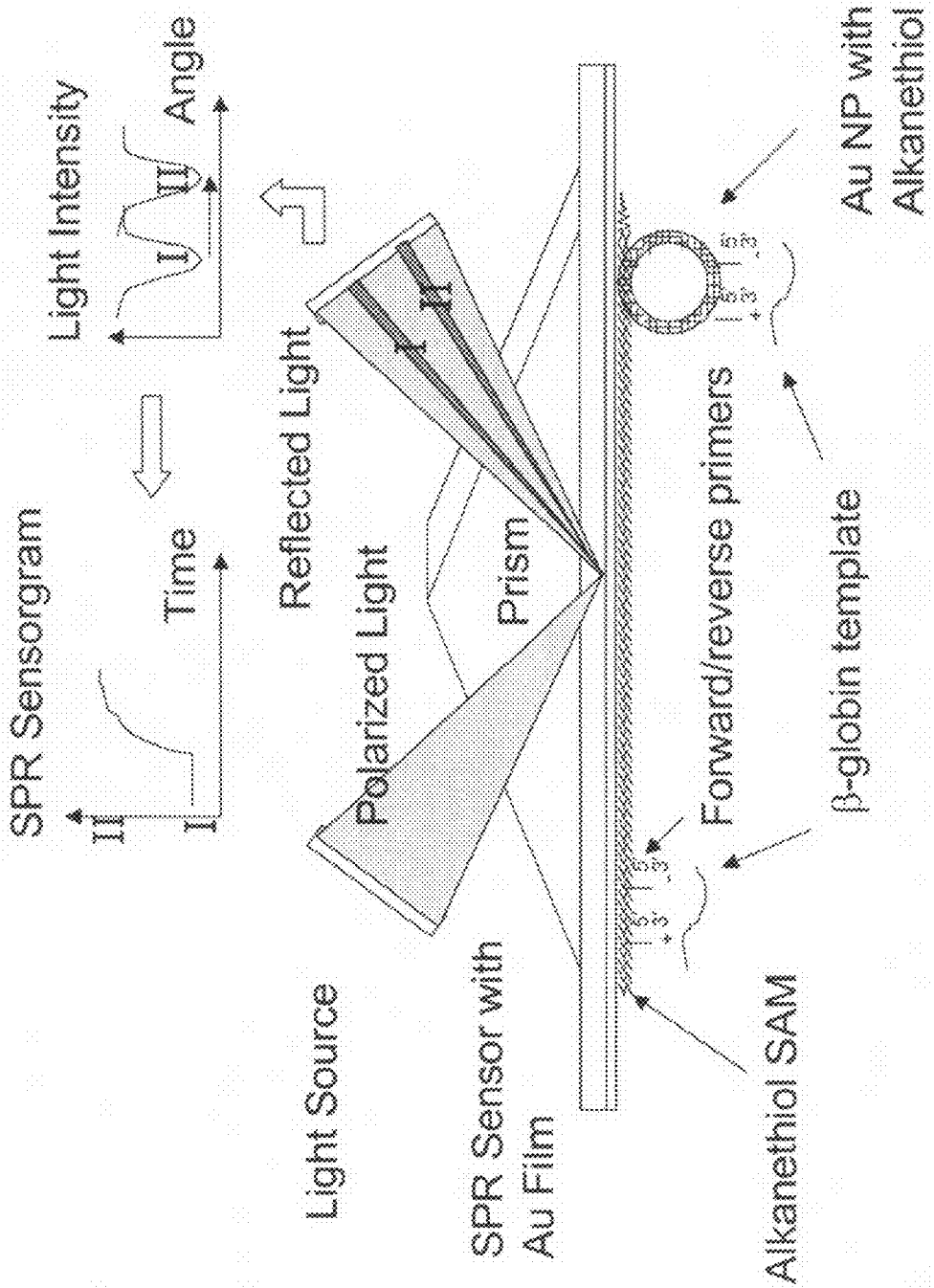
FIG. 1. SPR detection of β-globin template by immobilized forward/reverse primers FIG. 2. Spectral features of Au nanoparticles (Mie Scattering).

In one exemplary embodiment of the invention, label-free detection of PCR amplicons at picomolar levels by SPR may be used to quantify copy number kinetically while eliminating preparation and use of dyes or probes required for fluorescent detection. Direct, picosecond thermal dissipation in polynucleotide (e.g. DNA) samples induced by an optical source eliminates finite heat-transfer and conduction rates in conductive fluid and solid barriers between heat sources and DNA samples that limit cycling rates of block thermal cyclers and Lightcyclers™. Simultaneous SPR detection and thermal cycling are well-suited to high-throughput solid-phase extension, amplification and capture, which allows multiplex amplification using multiple bound primers and eliminates unequal amplification efficiencies, primer-artifact interference and cross-contamination of samples with amplified polynucleotide (e.g. DNA).

In certain embodiments heating with an optical source may comprise indirectly heating. For example, the optical source may be used to heat another or different element, which itself may transfer heat to the PCR reaction. In addition, other sources of heat may be used in connection or conjunction with the optical source so as to provide heat to a PCR reaction In certain embodiments of the invention, SPR-active Au surfaces with either immobilized polymerase or forward/reverse primer pairs catalyzed using N-hydroxysuccinimde (NHS) to covalently link free terminal primary amines on the polymerase or on modified oligonucleotide thymines, respectively, to a terminal carboxyl group of an alkanethiol on the Au surface with resonant absorption at wavelengths in the range 500 to 700 nm. Further, Taq polymerase and Phusion™ polymerase can be immobilized on Au surfaces using methods analogous to those used to covalently bond diethylethylenediamine to alkanethiol groups on Au (Roper & Nakra, 2004).

In certain embodiments of the invention, (1) rates and magnitudes of interactions between fragments from human genomic DNA template and immobilized Taq or Phusion™ polymerase or forward/reverse polynucleotide (e.g. DNA) primer pairs, respectively, are analyzed by monitoring mass-induced refractive index changes at resonance absorption with SPR; and (2) amplification efficiencies of either bound polymerase or primer between 1.2 and 1.9 (the efficiency of solution-phase amplification) are calculated by measuring fluorescence resonance enhanced transfer (FRET) from donor 3'-fluorescein to acceptor 5'-LC Red 640 on adjacent hybridization probes complementary to fragments of DNA at serial 10-fold dilutions from 105 to 10 copies of human genomic DNA template.

In certain embodiments of the invention, the temperature (T) adjacent to the Au surface can be cycled from 55° C. (primer anneals to template) to 72° C. (elongation by polymerase) to 94° C. (strands denature) within milliseconds using an optical source. One non-limiting example of an optical source includes an amplified Titanium:Sapphire laser system (tunable 600-3000 nm; 50 fs pulse duration; 50 µJ per pulse) to generate 390 nm pump pulses with 0.2 µJ/pulse intensity and a spot size of $6 \times 10^{-4}$ cm$^2$, or using a continuous Argon-ion laser system (1W). Ti:sapphire laser pumping can achieve for example, $\Delta T=17$ K and $\Delta T=39$ K, required for elongation and denaturation, respectively, relative to an ambient temperature of 55° C. without inactivating Taq or Phusion™ polymerase and that these temperature changes can be maintained for the required time-scale over characteristic lengths from 44 to 189 nm. Similarly, Argon-ion lasing can produce a total heat of $2.9 \times 10^{-3}$ J, which is required to achieve $\Delta T=17$ K elongation temperature for samples contained in Au-plated chambers insulated from their surroundings and which can be delivered in about 7 milliseconds. Characteristic decay times of 10 to 380 ps allows for millisecond thermal cycling of PCR-active molecules in solution adjacent to the Au surface. Calibrated changes in refractive index (RI) adjacent to the Au surface due to $\Delta T$ will be used to monitor T, providing an experimental control. Further, temperature, NaCl content and spacer length SPR-induced PCR amplification and detection using Au-immobilized primers and probe can be optimized using statistical factorial design (SFD), based on previous results from SFD in our group (Roper et al., 1999).

In certain embodiments of the invention, deoxyribonucleoside triphosphate (dNTP) addition and hybridization of DNA fragments to adjacent immobilized primers or probes are detected label-free in real-time, using a probe split from 10% of the Ti:Sapphire beam to monitor mass-dependent changes

EXAMPLES

Example 1

Synthesis and Derivatization of SPR-Active Surfaces for DNA Amplification

SPR-active Au surfaces with either immobilized Taq or Phusion™ polymerase or forward/reverse primer pairs PC03/PC04 and RS42/KM29 are catalyzed using N-hydroxysuccinimde (NHS) to covalently link free terminal primary amines on the polymerase or on modified oligonucleotide thymines, respectively, to a terminal carboxyl group of an alkanethiol SAM on the Au surface with a resonant absorption from 500 to 700 nm. The fraction of diluent alkane-thiol that eliminates nonspecific binding to Au surfaces was identified while maximizing accessibility. Red-shifts in extinction maxima of derivatized Au surfaces are determined to establish detection wavelength ranges.

Figure 2:
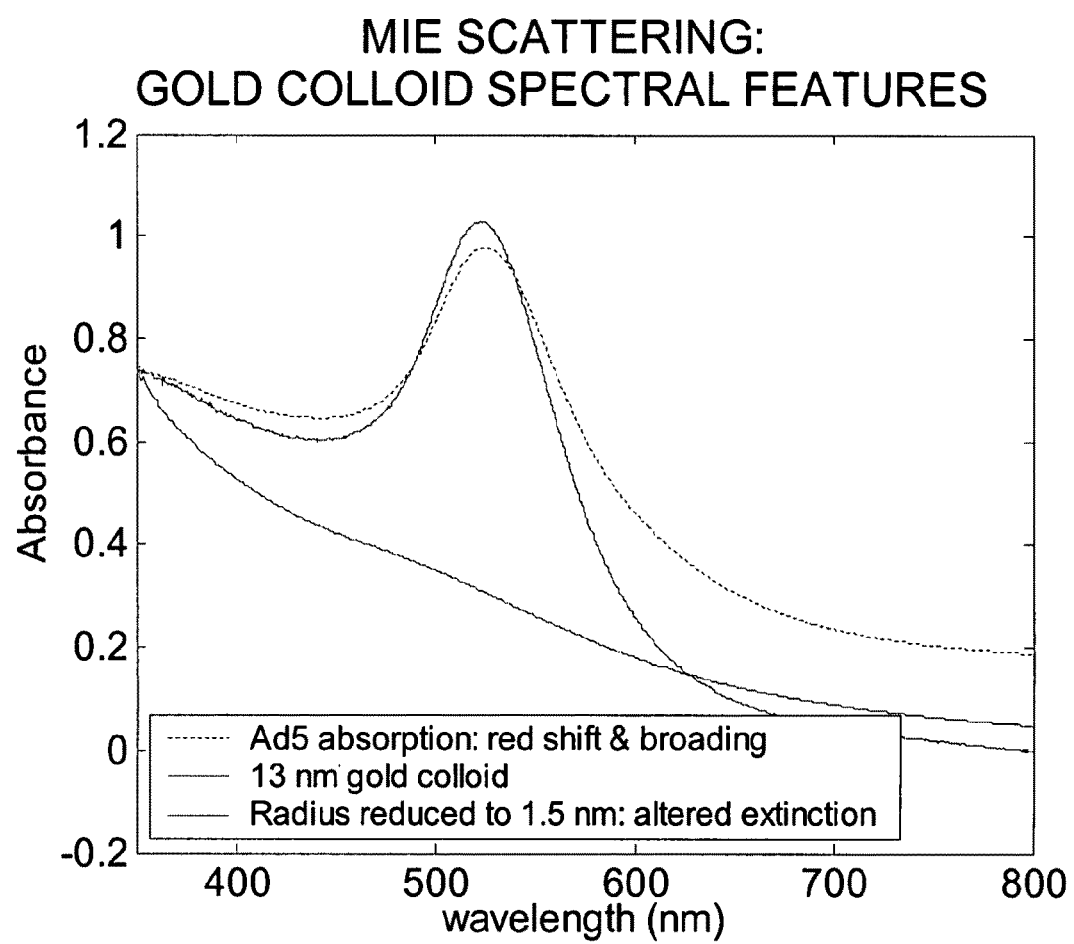
Figure 3:
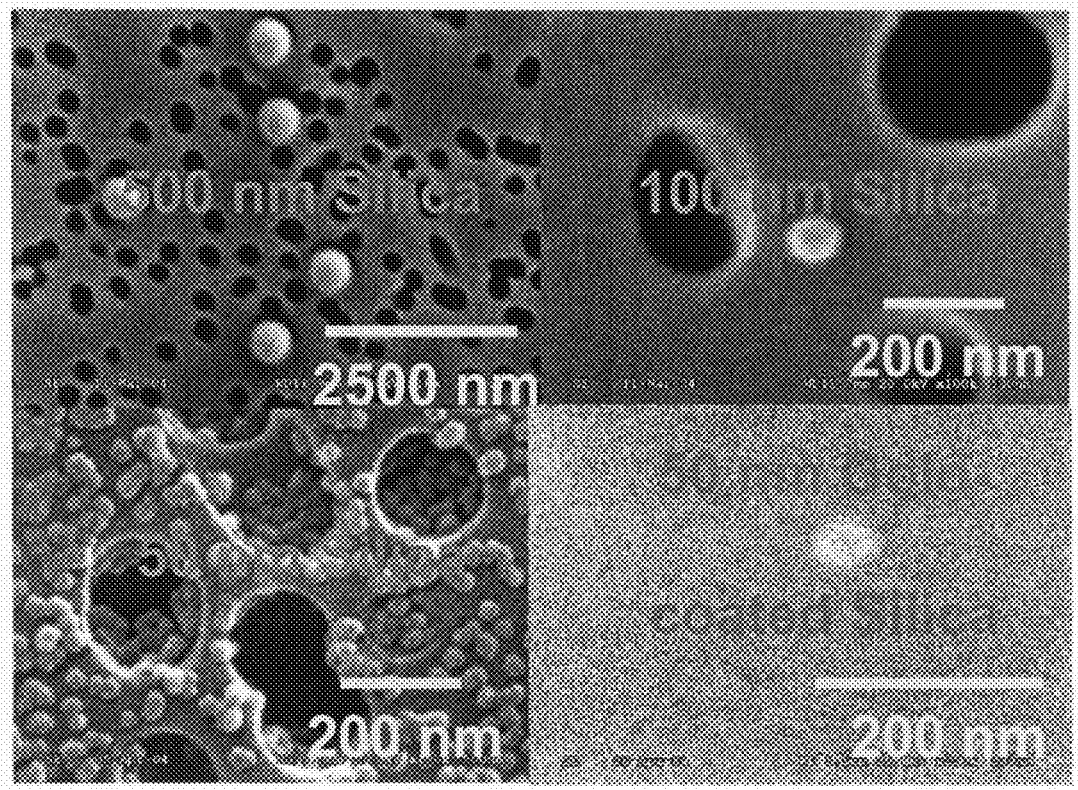
FIG. 3. Silica and Au-coated silica NP.

Au NP of 13-nm and 1.5-nm diameters were synthesized using procedures by Frens (1973) and Duff and Baiker (1993), respectively. FIG. 2 shows strong absorption at about 520 nm for an aqueous sol of 13-nm Au NP (solid line with peak), but no absorption for 1.5-nm colloidal gold NP (flatter solid line). Adsorption of adenovirus Type 5 to the 13-nm Au NP red-shifted and broadened the UV-vis absorbance spectra (dashed line). 1.5-nm Au NP was used to coat 50-nm silica NP that was synthesized to form Au—Si nanoshells. Nanoshells exhibit extinction maxima in the near-infrared region, which could extend SPR-induced DNA amplification and detection to optically opaque, complex biological fluids, cells or tissues. FIG. 3 shows SEMS of Au-coated Si nanoshells and uncoated Si NP between 50 and 500 nm on 0.2-μm pore membrane.

Synthesis of Au Surfaces: Planar and NP Au surface synthesized are illustrated in FIGS. 1 and 3. All chemicals may be obtained from Sigma (St. Louis, Mo.) unless otherwise noted. Briefly, planar Au surfaces (Spreeta) are be cleaned with 0.1 M NaOH and 1% Triton, then equilibrated in 10 mM MES buffer, pH 5.0 (3.0 ml/h). Au NP (13-nm or larger) are synthesized by trisodium citrate reduction of gold tetrachloroaurate using the method of Frens (1973). Briefly, 100 mL of 1 mM HAuCl$_4$ may be brought to a vigorous boil with stirring in round-bottom flask with reflux condenser. 10 mL of 38.8 mM sodium citrate may be rapidly added. The solution may be boiled for 15 minutes. Color changes from pale yellow to deep red after 2 min. Au NP suspensions remain stable for weeks when stored at 4° C.

Self-Assembled Monolayer Formation: Self-Assembled Monolayer (SAM) formation is outlined in FIG. 4. Diethylethylenediamine (DEEDA) may be replaced herein by primer or polymerase. Briefly, planar Au surfaces are equilibrated in degassed ethanol, as previously reported (Roper and Nakra, 2004), then exposed to 2.0 mM 11-mercaptoundecanoic acid (MUDA) in degassed ethanol until refractive index stabilized (6-24 hrs; 0.1 ml/h). The SAM of MUDA may be rinsed with ethanol (0.6 ml/h), then 10 mM 2-morpholinoethanesulfonic acid, monohydrate (MES) buffer, pH 5.0, (3.0 ml/h) until refractive index stabilizes. Freshly prepared solutions of 0.4 M N'-(ethylcarbonimidoyl)-N,N-dimethylpropane-1,3-diamine hydrochloride (EDAC) and 1.0 M N-hydroxysuccinimide (NHS) in 10 mM MES are mixed 1:1 and injected for 20 minutes (3.0 ml/h) to prepare the terminal carboxyl group for amide bond formation. Au NPs are stabilized against aggregation by adsorption of polysorbate-20 (PS-20), then place-exchanged with MUDA to form the SAM.

Derivatization with Polymerase or Primers: Polymerase or primer takes the place of DEEDA in FIG. 4. To form amide bonds between free terminal primary amines on Taq (Perkin Elmer) or Phusion™ polymerase (Phusion) and SAM carboxyl groups, polymerase will be dissolved in 0.01 M MES buffer, pH 5 (25° C.), then contacted with the surface for 0.75-2 hrs (3.0 ml/h). To immobilize forward/reverse primer pairs PC03/PC04 and RS42/KM29 (Roche), a 5' thymine on a base may be modified with a C6 primary amine to provide amide bonding with the terminal carboxyl group of MUDA-SAM. Exemplary forward/reverse primer pairs are tabulated below. Alternatively, 5' disulfide bonds of alkanethiol-capped oligos are cleaved to permit Au-thiol covalent bond formation. Derivatized surfaces are then be rinsed with 10 mM MES buffer at pH 5 (25° C.) and then at pH 6.7 (25° C.). FIG. 1 illustrates primers derivatized onto planar and NP Au surfaces.

| Fragment | Forward Primer | Reverse Primer | Reference |
|---|---|---|---|
| 110-bp | d(ACACAACTGTGTTCACTAGC) (SEQ ID NO: 1) | d(CAACTTCATCCACGTTCACC) (SEQ ID NO: 2) | (Takara) |
| 536-bp | d(GCTCACTCAGTGTGGCAAAG) (SEQ ID NO: 3) | d(GGTTGGCCAATCTACTCCCAGG) (SEQ ID NO: 4) | (Takara) |

Figure 4:
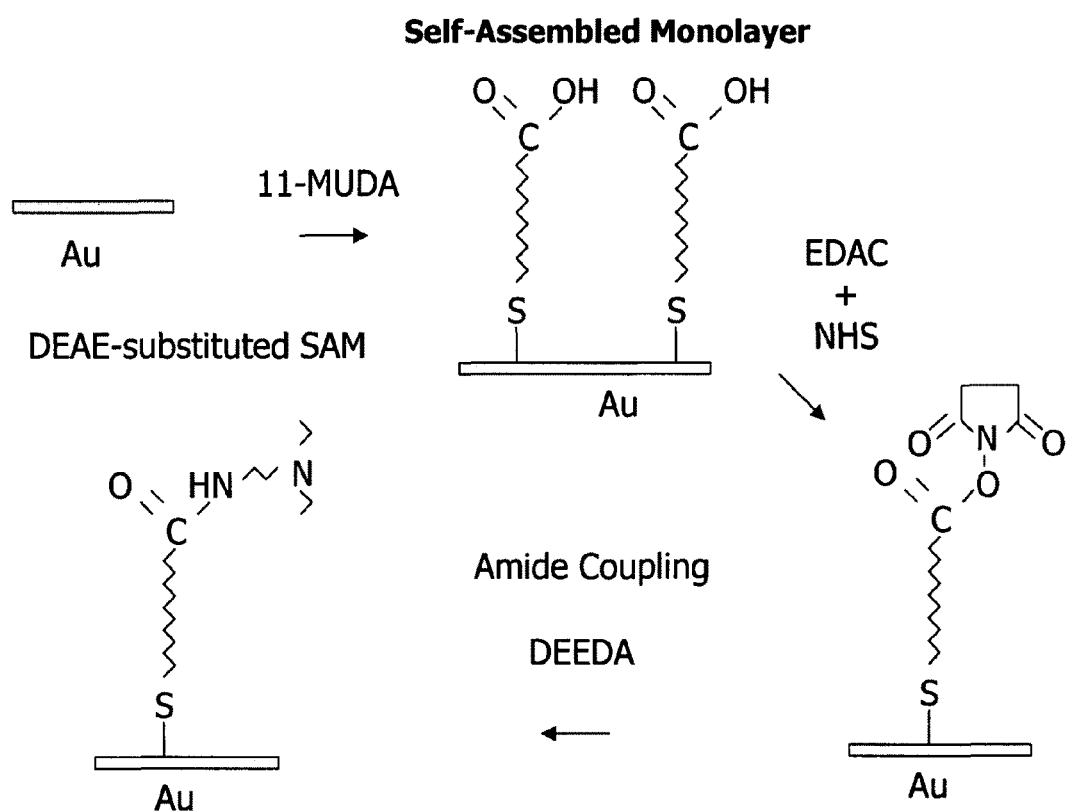
FIG. 4. Self-assembly of alkanethiol on Au and subsequent derivatization.

Au surfaces were derivatized with a carboxyl-terminated alkanethiol, 11-mercaptoundecanoic acid (11-MUDA), (after first absorbing polysorbate on the Au NP) to form self assembled monolayers (SAMs). A novel DEAE-terminal SAM was developed by linking N,N-diethylethylenediamine (DEEDA) to 11-MUDA using N-hydroxysuccinimide (NHS) and N'-(ethylcarbonimidoyl)-N,N-dimethylpropane-1,3-diamine hydrochloride (EDAC) to catalyze amide bond formation between a terminal carboxyl on MUDA a primary amine on DEEDA (Roper & Purdom, 2004). FIG. 4 shows the steps in the derivatization. In one aspect of the present invention, DEEDA may be replaced by polymerase or primers. SPR was used to monitor SAM derivatization showed stoichiometric yields of amide bond formation. UV-vis was used to monitor red shift at 550 nm during adsorption of Polysorbate 80 (PS-80) on 13-nm gold colloids (similar to FIG. 2). Place exchanging the PS-80 with 11-MUDA further red-shifted the absorbance. All 11-MUDA SAMs were stable to NaCl content from 0 to 1.0M. These methods are used to derivatize alkanethiol SAMs with Taq polymerase, Phusion™ polymerase and primer pairs PC03/PC04 and RS42/KM29 to amplify 110- and 536-bp β-globin fragments.

Optimization and Characterization: The fraction of thiolated diluents containing the linker, but not the primer are adjusted during derivatization to maximize accessibility of polymerase and primers, as measured by SPR and FRET. Au surfaces are monitored by SPR during derivatization to confirm yield and stoichiometry of immobilization. UV-vis spectra of Au surfaces may be used to identify derivatization-induced red-shifts in extinction maxima for 13, 30 and 50 nm Au NP, which are normally $\lambda_{max}$=520, 528 and 540 nm, respectively. Red shifts similar to the shift from flatter solid line to the dashed line in FIG. 2 are seen.

Example 2

Characterization of Immobilized Polymerase and Primer

Figure 5:
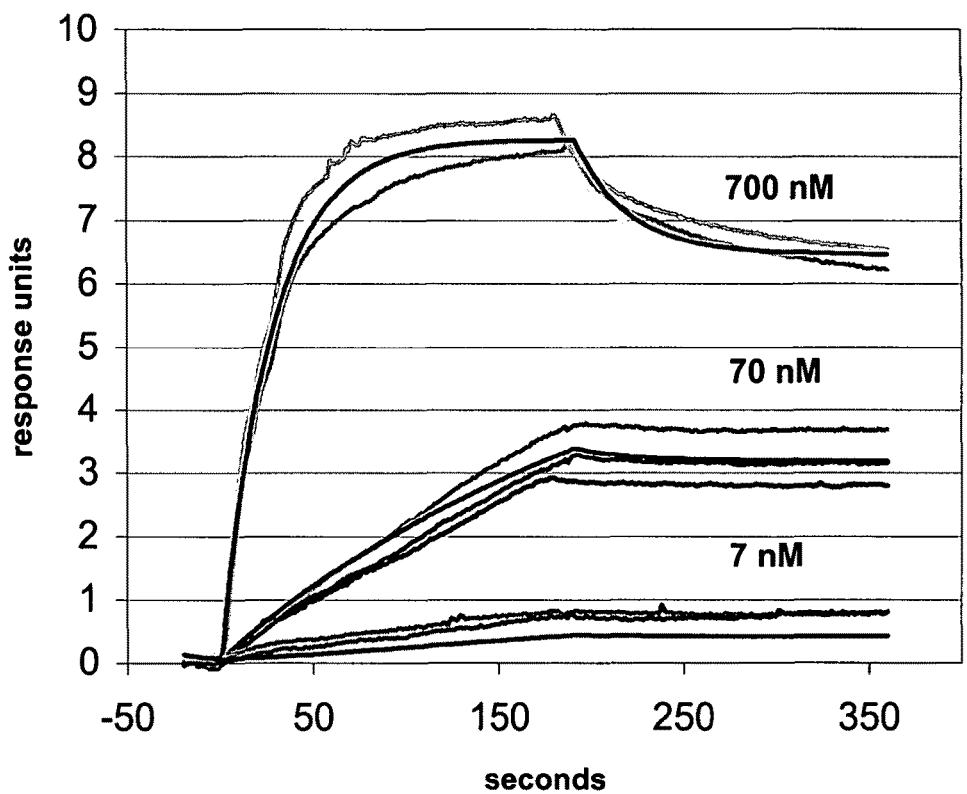
FIG. 5. Binding of cytochrome c to Au-SAM.
Figure 6:
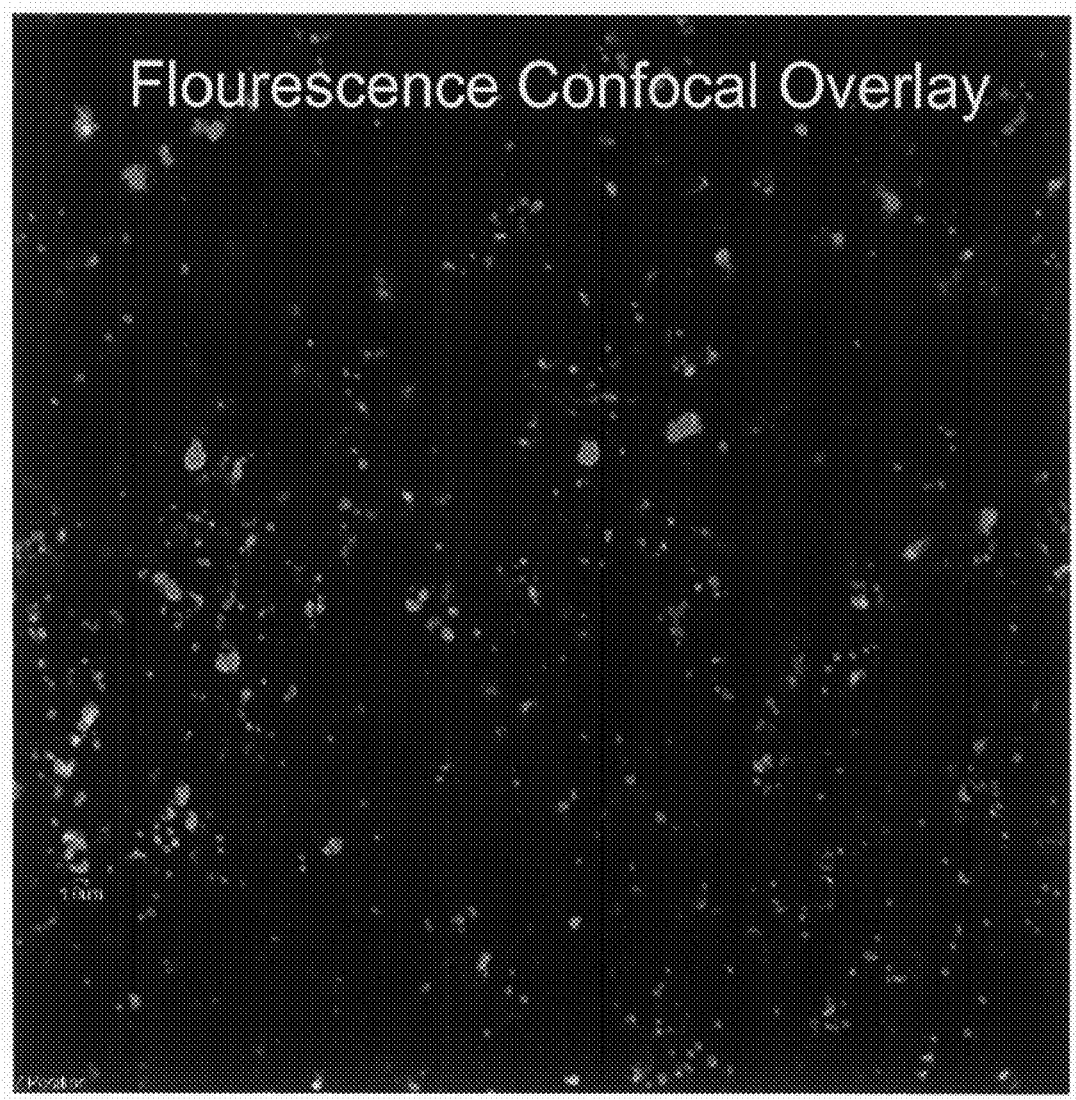
FIG. 6. LSCM of Far-red labeled NP binding to Oregon-Green labeled polymer.

Characterization of immobilized proteins by SPR and Fluorescence Methods Immobilization rates and surface coverage of cytochrome c on alkanethiol-derivatized Au surfaces were characterized (Roper & Nakra, 2004) and imaged fluorescent-labeled particles. FIG. 5 is a SPR sensorgram that shows cytochrome c sorption onto a derivatized alkanethiol SAM. The sensorgram data was fit to a 2-compartment mass transport limited reaction model using CLAMP software (Center for Biomolecular Interaction Analysis, University of Utah) to estimate sorption rate constants, $k_f$=6.9±0.053×10$^4$ M$^{-1}$ s$^{-1}$ and $k_r$=1.8±0.033×10$^{-3}$ s$^{-1}$. Measured surface coverage was ⅔ of the random sequential adsorption limit of 1.4 ng cytochrome c per mm$^2$ calculated from a hard sphere model. FIG. 6 shows a krypton/argon laser (488/647 nm) scanning fluorescence confocal overlay of Far-Red-labeled 175-nm anionic NP interacting electrostatically with Oregon-Green-labeled sintered cationic polymer. Ad5 was also labeled with fluorescent Texas-Red-X to image its dielectrophoresis. The methods developed in these efforts are extended to immobilize polymerase and primer on the Au surface and characterize PCR by FRET using fluorescent-labeled hybridization probes.

Rates and magnitudes of interactions between β-globin fragments from human genomic DNA template and immobilized Taq polymerase or forward/reverse primer pairs PC03/PC04 and RS42/KM29, respectively, can be quantified by monitoring mass-induced RI changes at resonance absorption with SPR. Amplification efficiencies of either bound polymerase or primer between 1.2 and 1.9, which is efficiency of solution-phase amplification, can be calculated by measuring fluorescence resonance enhanced transfer (FRET) from donor 3'-fluorescein to acceptor 5'-LC Red 640 on adjacent hybridization probes complementary to 110- and 536-bp fragments of β-globin at serial 10-fold dilutions from 10$^5$ to 10 copies of human genomic DNA template. SPR may be used to measure interaction rates and surface coverages for β-globin template interacting with immobilized polymerase and primers and FRET to measure amplification efficiencies between 1.2 and 1.9. These results may be used to optimize template length and/or genomic DNA denaturation conditions as well as to optimize NaCl content, temperature and cycle times for solid phase amplification using factorial designed experiments.

DNA Amplification: Au-immobilized polymerase and primer pairs are each characterized in separate experiments. Briefly, DNA may be amplified in 50 mM Tris-HCl, pH 8.5 (25° C.), 3 mM MgCl$_2$, 500 μg/mL bovine serum albumin, 0.2 μM of each β-globin primer, 200 μM of each deoxyribonucleoside triphosphate dNTP (Perkin Elmer), and 0.2 U of Taq DNA polymerase (Perkin Elmer), per sample unless otherwise stated. Experiments using immobilized polymerase or primer pairs will have these components subtracted from the mix. Human genomic DNA (denatured by boiling for 1 min) may be used as DNA template. In block cyclers the amplification cycle will consist of 94° C. for 15', then 35 cycles of 94° C. denaturation for 1', 55° C. annealing for 1' and 72° C. extension for 1' 30 s, ending with 72° C. for 8'. Light-cycling will use 45 cycles of 94° C. denaturation for 0 s, 55° C. annealing for 10 s and 72° C. extension for 5 s (Caplin et al., 1999). Statistical factorial design (SFD) may be used, as previously reported (Roper et al., 1999), to identify concentrations of MgCl$_2$, NaCl, and temperature that optimize amplification.

Template DNA Interaction Analysis: Rates and magnitudes of β-globin template interaction with Au-immobilized forward/reverse primer pairs PC03/PC04 and RS42/KM29 are determined from SPR sensorgrams using the 2-compartment mass transport limited reaction model (Roper 2004c). Rates and magnitudes of β-globin template plus primer interacting with Au-immobilized Taq polymerase and Phusion™ polymerase, respectively, are likewise determined. SPR sensorgrams similar to FIG. 5 are seen for both these interactions. Efficiency of Au-NP immobilized surfaces may be characterized in a thermal cycler and compared with control tubes. Planar-Au surfaces are characterized in situ in an SPR flow cell by cycling flow temperature. Amplification efficiencies, E=exp(ln 10/−s)−1, are calculated from the slope, s, of a standard curve constructed from threshold cycle ($C_t$) values that correspond to serial dilutions of 10$^5$, 10$^4$, 10$^3$, 10$^2$ and 10 copies of template used to initiate PCR. $C_t$ values are measured at 10-fold serial dilutions from 10$^5$ to 10 copies of human genomic DNA template using FRET from donor 3'-fluorescein to adjacent acceptor 5'-LC Red 640 labels on 23-35 bp hybridization probes complementary to 110- and 536-bp fragments of β-globin (Roche). Maximum absorbance/emission wavelengths for 3'-fluorescein and 5'-LC Red 640 are λ=494/524 nm ($\epsilon_{494,dye}$=6.8×10$^4$M$^{-1}$ cm$^{-1}$) and λ=622/638 nm ($\epsilon_{622,dye}$=1.1×10$^5$M$^{-1}$ cm$^{-1}$). Absorbance at 260 nm is 25-33% of these values.

Example 3

Induction of SPR Thermal Cycling

Preliminary Studies to Induce SPR thermal cycling: A method to determine operating conditions for a Ti:Sapphire laser system (tunable 600-3000 nm; 50-fs pulse duration; 50-μJ per pulse) was devised to achieve temperature increases for characteristic length and time scales required to amplify and denature a 110-bp β-globin gene fragment. It indicates only 3×0.2-μJ laser pulses are required (over 4 ms, at ω=1 kHz) to raise ΔT=17 over a length of 91 nm from the Au surface. The method may be used to determine necessary heat input for any template using its characteristic temperature, length and time scales.

Pulsed-Laser Energy Input: Briefly, Fourier number (Fo) relates thermal dissipation length to characteristic dissipation time: $1_d$=(4α$\tau_d$/Fo)$^{1/2}$ (Carslaw & Jaeger, 1959; Incropera & Dewitt, 1985). Aqueous suspensions of 2R=50-nm Au particles pulsed at 390 nm exhibit $\tau_d$~380 ps, independent of ΔT (and pulse energy) between 40 K and 160 K (Hu & Hartland, 2002). A first-order estimate of a pulse penetration length may be made assuming Fo~1 and using α=k$\rho_f^{-1}$ $C_f^{-1}$=(0.650 W m$^{-1}$K$^{-1}$/(1 g cm$^{-3}$*4.184 J g$^{-1}$K$^{-1}$)=0.00155 cm$^2$ s$^{-1}$ to give $1_d$=7.7 nm. This is ~17% of a thermal dissipation length of 44 nm. The heat, $Q_{surr}$, required to achieve ΔT=17 k in spherical aqueous shells of radius r-r' surrounding Au NP of radius r'=50 nm at a concentration [Au]=1.2×10$^{-4}$M or a number density $n_{Au}$=2.3×10$^{12}$ NP per liter and a characteristic thermal dissipation radius r=91 nm for a total (spot-size cylindrical) volume, V~1.2×10⁻⁷ L, is:

$$Q_{surr} = \frac{4\pi \Delta T \rho_{H2O} C_{H2O} n_{Au} V}{3}(r^3 - r'^3) \quad (5)$$

Eq. 5 gives $Q_{surr}$=0.05×10⁻⁶ J using $C_{H2O}$=4.184 J g⁻¹K⁻¹ and $\rho_{H2O}$=1 g cm⁻³. Eq. 1 showed τ=9.6% of applied laser energy is absorbed by the NP, so $Q_{surr}$ can be delivered in ~0.003 sec by about 2.7×0.2 µJ pulses at ω=1 kHz. Eq. 5 also gives the heat, $Q_{Au}$, required to achieve ΔT=17K in Au spheres of radius r'=50 nm at a concentration [Au]=1.2×10⁻⁴ M for a total volume, V~1.2×10⁻⁷ L by substituting $C_{Au}$=0.129 J g⁻¹K⁻¹ for $C_{H2O}$, $\tau_{Au}$=19.3 g cm⁻³, for $\tau_{H2O}$, and r'³ for (r-r'³). This gives $Q_{Au}$=0.006×10⁻⁶ J, which can be delivered in 0.001 sec by 0.3×0.2 µJ pulses at ω=1 kHz. Thus the total heat required to achieve ΔT=17K elongation temperature for spot-size sample of Au-template insulated from its surroundings is ~0.056×10⁻⁶ J, which can be delivered in about 0.004 seconds.

Determining Continuous-Laser Power Requirements: Power requirement was estimated using the Fourier number (Fo), which relates characteristic dissipation time, $\tau_d$, to thermal dissipation length: $\tau_d$=(Fo)$l_d^2$/4α where α is thermal diffusivity (Carslaw & Jaeger, 1959; Incropera & Dewitt, 1985). As a basis it was considered that a 2-cm long 0.2-µm thick Au layer can absorb 40% of high-power multiwavelength Ar-ion laser light (0.1-4 W) (McMillen et al., 2005). First-order estimates of $\tau_d$ in radial and axial directions may be made for a cylindrical cavity of diameter $1_d$=13×10⁻⁴ cm and length L=2±0.1 cm assuming Fo~1 and using an aqueous value of α=k $\tau_f^{-1}$ $C_f^{-1}$=(0.650 W m⁻¹K⁻¹/(1 g cm⁻³*4.184 J g⁻¹K⁻¹)=0.00155 cm² s⁻¹. This gives $\tau_d$=0.27 milliseconds (radial) and $\tau_d$=1.6 seconds (axial). The heat, $Q_{sample}$, required to achieve ΔT=17K in a cylindrical samples of radius $1_d$/2=6.5×10⁻⁴ cm and length L=2 cm within annular Au coating of thickness r'Z-r=6×10⁻⁷ cm with 6-fold symmetry giving a total cylindrical sample volume, V~1.6×10⁻⁵ milliliters, is:

$$Q_{sample} = \Delta T \tau_{H2O} C_{H2O} V \quad (6)$$

Eq. 6 gives $Q_{sample}$=1.1×10⁻³ J using $C_{H2O}$=4.184 J g⁻¹K⁻¹ and $\tau_{H2O}$=1 g cm⁻³. Assuming the Au coat transduces 40% of applied laser energy means $Q_{sample}$ can be delivered in ~3 milliseconds using a 1-W laser source. Eq. 6 was also used to determine the heat, $Q_{Au}$, required to achieve ΔT=17K in an annular cylindrical Au coating of thickness 6×10⁻⁷ cm with 5-fold symmetry for a total volume, V~2.9×10⁻⁸ milliliters by substituting $C_{Au}$=0.129 J g⁻¹K⁻¹ for $C_{H2O}$ and $\tau_{Au}$=19.3 g cm⁻³. This gave $Q_{Au}$=1.2×10⁻⁶ J, which can be delivered in 3 microseconds by the 1-W laser. Since the thermal dissipation length for silica in 0.9 milliseconds is 0.005 cm given a thermal diffusivity of 7.5×10⁻³ cm²/s, the $Q_{MOF}$ required for a Si fiber volume of 5.7×10⁻⁵ milliliters is 1.8×10⁻³ J. Thus, the total heat required to achieve ΔT=17K elongation temperature for sample contained in these Au-coated cylinders insulated from their surroundings is 2.9×10⁻³ J, which can be delivered in about 7 milliseconds.

Thermal cycling on Au NP with Ti:Sapphire laser: Local RI changes due to T in the derivatized system will be first be determined, so local T can be monitored by SPR during thermal cycling. Output from an amplified, tunable Ti:Sapphire laser system (tunable 600-3000 nm; 50 fs pulse duration; 50 µJ per pulse) are split 90/10 by a beam splitter to supply pump and probe pulses. The larger portion (~90%) may be manipulated to generate ~390 nm pump pulses. The intensity of these pulses may be controlled with a λ/2-waveplate/polarizer combination to give ~with a spot size of ~6×10⁻⁴ cm². The smaller portion (~10%) may be used to generate the probe. A stepper motor will control timing between the pump and probe pulses. Pump powers and repetition rate are modulated to provide a heat flux by dissipative electron-phonon coupling that sustains the target temperature at the point of the covalently linked template DNA, as given by Eqs 5 and 6. Briefly, for 110-bp β-globin, T will increase from 55° C. (annealing for 1 s) to 72° C. (elongation for 66 ms) using 3×0.2 µJ pulses (takes only 4 ms), then to 94° C. (denaturation for 1 s). Pulse rate and time at each T may be optimized by SFD.

Thermal cycling on Planar Au Surfaces: A monolayer of Au NP may be spun-coat onto planar Au to achieve thermal cycling. Briefly, Au NP may be dissolved in EtOH (0.05% w/v) and spun coated (2000 rpm) from a glass pipette (3×250 uL droplets) centrally, at a height of 5 mm above the spinning slide. Uniformity and thickness of the deposited NP monolayer may be confirmed by SEM. SEM images of Si and Au—Si NP are seen in FIG. 3.

Temperature (T) can be cycled from 55° C. (primer anneals to β-globin template) to 72° C. (elongation by polymerase) to 94° C. (strands denature) within milliseconds using an amplified Titanium:Sapphire laser system (tunable 600-3000 nm; 50 fs pulse duration; 50 µJ per pulse) to generate 390 nm pump pulses with 0.2 µJ/pulse intensity and a spot size of 6×10⁻⁴ cm². Calibrated changes in refractive index (RI) adjacent to the Au surface vs. T will be used to monitor local T, providing an experimental control. The three model equations are refined based on this data: laser parameters that control thermal excitation and dissipation, cycling time constants, and the phenomenological model for T distribution.

Thermal cycling within Au-coated cylinders using continuous Ar-ion laser: Local RI changes due to T in the derivatized system may be first be determined, so local T can be monitored by SPR during thermal cycling. Output from the continuous Ar-ion laser system may be split 90/10 by a beam splitter to supply pump and probe pulses. The larger portion (~90%) may be manipulated to generate high power pump pulses. The smaller portion (~10%) may be used to generate the probe. A stepper motor controls timing between the pump and probe pulses. Pump power may be modulated to provide a heat flux by dissipative electron-phonon coupling that sustains the target temperature at the point of the covalently linked template DNA, as given by Eq 5. Briefly, for 110-bp β-globin, T increases from 55° C. (annealing for 1 s) to 72° C. (elongation for 66 ms) using 7 milliseconds of 1-W power, then to 94° C. (denaturation for 1 s) using an additional 9 milliseconds of 1-W power. Power and application time at each T are optimized by SFD.

Figure 9:
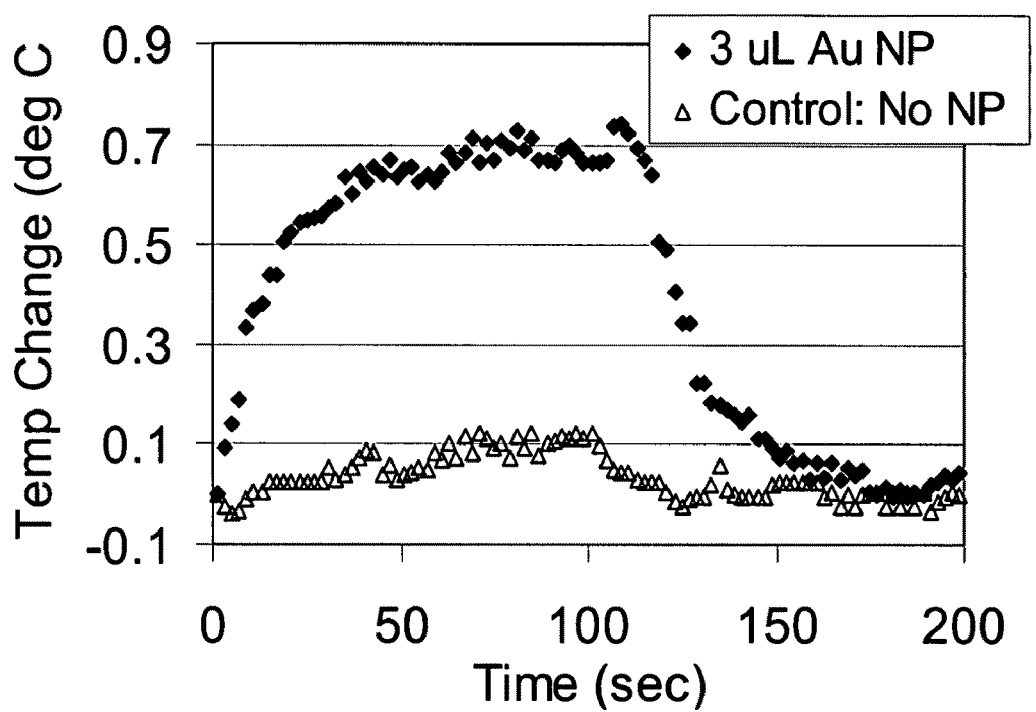
FIG. 9. Graph of Thermal Cycling using Argon-ion laser induction of SPR on Au NP.

Thermal Cycling Results using Ar-Ion Laser: A 3-microliter aqueous solution of 1×10⁻⁹ M Au NP was exposed to 0.5 W continuous wave argon ion laser (nm) within an evacuated chamber at 130-mTorr and observed a ΔT of +0.6° C. relative to the same sample chamber exposed to the beam without NP under identical conditions. Data are shown in FIG. 9. At steady state, total heat flux from the sample, $Q_{Tot}$, was 1.6×10⁻⁴ W. This corresponds to transduction of 0.016% of energy from a 1 W laser beam. A heat flux of 1×10⁻⁴ W was conducted via 0.75 inches air at 0.3 Torr surrounding a sample chamber with outer dimensions 0.6×4.4×12 mm (thickness× width×height) for a total heat-transfer area of 6.3×10⁻⁵ m², using thermal conductivities of $k_{air}^{1\ atm}$=2.36×10⁻² W/mK' and $k_{air}^{0.3\ Torr}$=7.89×10⁻³ W/mK. A heat flux of 6×10⁻⁵ W was conducted via two 2-inch long thermocouples (TC) of $OD_{TC}$=0.003 inches giving a total cross-sectional area of $9 \times 10^{-9}$ m², using thermal conductivities of $k_{chromium}$=94 K W/mK and $k_{aluminum}$=237 W/mK. Using $OD_{TC}$=0.0005 inches would reduce $Q_{Tot}$ by ⅓ to $1.05 \times 10^{-4}$ W. Transduction of CW laser by NP in this preliminary system was 0.04% of the total power input, likely due to observable Au NP precipitation, consistent with literature reports (Schmid et al., 1987). These results verify Au transduction of laser light Example 4

Detection of DNA Elongation and Amplification

Figure 7:
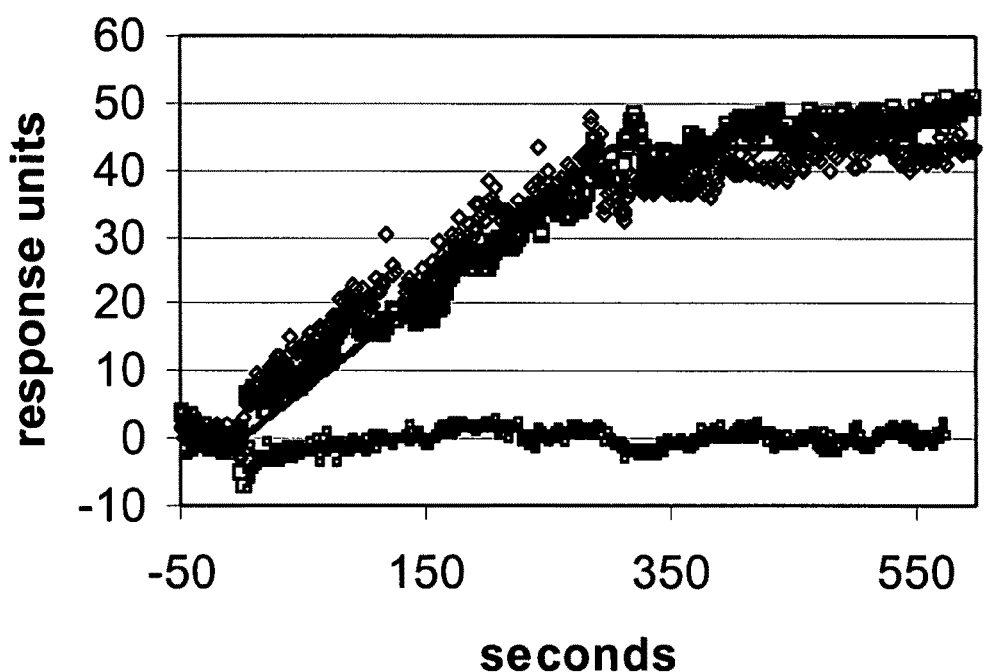
FIG. 7. Graph of SPR sensorgram of Ad5 binding to Au-SAM.
Figure 8:
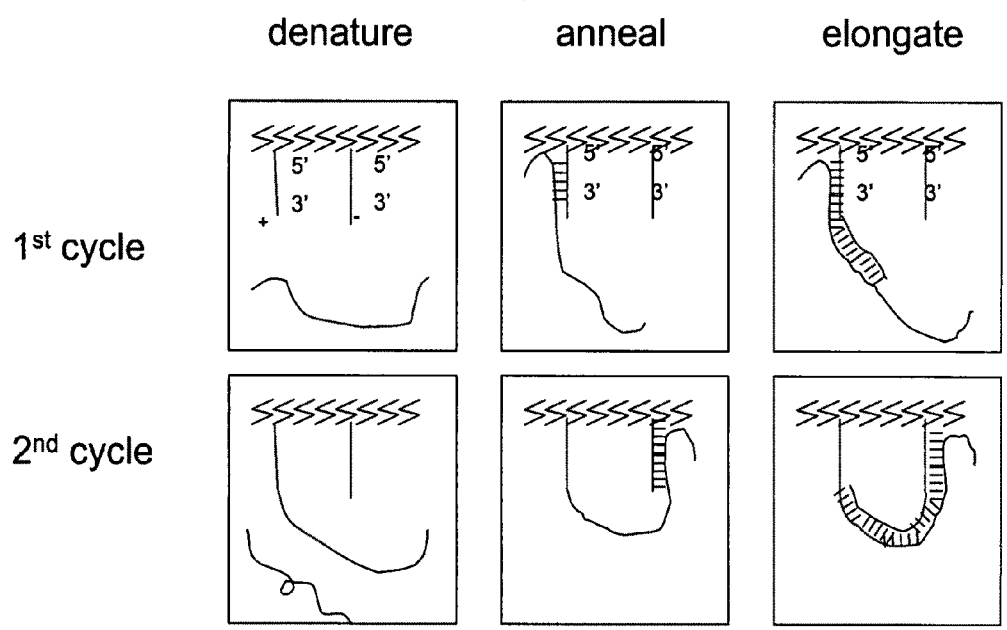
FIG. 8. Amplification and detection with immobilized primer pairs.

Picomolar and femtomolar concentrations of adenovirus Type 5 (Ad5) were detected using SPR (Roper & Nakra, 2004) and identified optimum pulsed-laser extinction values and probe sizes to detect alkanethiol-capped oligonucleotides immobilized on Au NP. FIG. 7 is a graph depicting SPR detection of 1.6 pM Ad5 interacting with DEAE-substituted Au-SAM. Rates of Ad5 interaction with the surface decreased as NaCl increased from 4.8 mM to 48 mM, consistent with a DLVO model that includes mass-transfer limited deposition and screening of electrostatic interactions. No cross-talk is expected between 390-nm laser-pump thermal excitation pulses and a probe split from the Ti:Sapphire beam detection, since absorption at 390 nm, $\epsilon_{390\,nm}$=2000 M$^{-1}$ cm$^{-1}$, is both relatively independent of particle radius in the range 2R=15-50 nm (Hu & Hartland, 2002) and ~5-7 logs lower than absorption for Au NP-bound alkanethiol-capped oligos: $\epsilon_{520}$=2.7×10⁸ M$^{-1}$ cm$^{-1}$ (2R=13 nm); $\epsilon_{528}$=3.7×10⁹ M$^{-1}$ cm$^{-1}$ (2R=30 nm); and $\epsilon_{540}$0=1.5×10¹⁰ M$^{-1}$ cm$^{-1}$ (2R=540 nm) (Jin et al., 2003). Tuning the probe to the maximum extinction for probe Au particles minimizes contributions from beat signals (Hartland, 2002). Alkanethiol-capped oligos bound to Au NP red-shift maximum extinction values to $\lambda_{max}$=520, 528 and 540 nm for 2R=13, 30 and 50 nm NP, respectively (Jin et al., 2003). For immobilized-polymerase systems, ~23-bp single-stranded probes can be used by performing asymmetric PCR (Kai et al., 1999). FIG. 8 schematically illustrates that adjacent forward and reverse primers serve as probes in immobilized primer-pair systems.

dNTP addition and hybridization of 110- and 536-bp β-globin fragments to adjacent immobilized primers or 23-bp probes ise detected without labels in real-time, using a probe split from 10% of the Ti:Sapphire beam to monitor mass-dependent changes in local refractive-index at wavelengths that extinction maxima of the Au surfaces. Results are correlated with FRET signal detected from hybridization probe binding to the fragments in experimental controls. Amplification of 110- and 536-bp fragments at efficiencies from 1.2 to 1.9 in 66 and 330 ms, respectively, occurs as well as detection of amplicons at femtomolar concentrations.

Detecting Elongation on Planar Au Surfaces: Briefly, a SPR integrated flow cell (Nomadics, Inc; Stillwater, Okla., USA) may be attached to a syringe pump from Cole Parmer, Inc (Vernon Hill, Ill., USA), via a manual polyethyletherketone (PEEK) injection valve from Upchurch, Inc (Oak Harbor, Wash., USA) using PEEK tubing and fittings. RI baselines are established in the PCR buffer as shown in FIG. 7. Human genome template, dNTPs and polymerase or primer are diluted into PCR buffer and injected 300 μl/min from a syringe in a second syringe pump for 3 minutes during thermal cycling. Rates of dNTP addition during elongation by Au-immobilized forward/reverse primer pairs PC03/PC04 and RS42/KM29 are determined from SPR sensorgrams (like those in FIGS. 5 and 8) using the 2-compartment model (Roper 2004c). Rates of dNTP addition during elongation by Au-immobilized Taq polymerase and Phusion™ polymerase, respectively, are similarly determined.

Detecting Copy Number Increases on Planar Au: Amplicon binding to Au-bound probes may be monitored in real-time to generate a SPR sensorgram, as shown in FIG. 1. In immobilized-primer systems, adjacent forward or reverse primers bind and amplify template DNA. FIG. 8 shows 3-steps in 2 cycles of solid-phase DNA amplification. In immobilized polymerase systems, short ~23-bp single-stranded oligonucleotide probes are immobilized on the Au surface to bind amplicons using results from Examples 1 and 2. Asymmetric PCR in these systems will allow these short probes to be used.

Detection on Au NP: Ten percent of the laser output may be used to generate a white light continuum to use as an optical probe. Wavelength ranges include extinction maxima of $\lambda_{max}$=520, 528 and 540 nm for 13, 30 and 50 nm Au NP, respectively, with red-shifts that were identified using UV-Vis. Bleach signal from thermally activated Au surfaces disappears within picoseconds. Real-time detection of elongation or amplification occurs by monitoring RI changes due to dNTP addition, or amplicon binding to immobilized primer pairs or probes, respectively. Amplification efficiencies, E=exp(ln 10/−s)−1, are measured for SPR-based PCR on planar and NP Au surfaces and compared with FRET signal detected from experimental controls.

Detection of DNA elongation and amplification from SPR-induced Thermal Dissipation: Results from Examples 2 and 3 permit analyzing effects of fragment length (110 vs. 536-bp), polymerase processivity (e.g., Taq vs Phusion™), Au surface (e.g., planar vs. spherical), immobilized ligand (e.g. primer pair vs. polymerase) on multiple outcomes including FRET amplification efficiency, SPR detectability (e.g., elongation vs. amplification) or SPR interaction (e.g., rate vs. magnitude). Factorial design may be applied to determine the magnitude of each effect as well as interactions between effects. A suitable design may be constructed to constructively evaluate the primary effects and interactions in a minimum of experiments. For example, a $2^3$ design could determine effects of fragment length, polymerase processivity and immobilized ligand on amplification efficiency.

Detection of DNA elongation and amplification: A gold surface-plasmon-resonance active sensor surface or gold nanoparticle surface may be derivatized with carboxyl-terminated alkanethiol. N-hydroxysuccinimide and N'(ethylcarbonimidoyl)-N,N-dimethylpropatne-1,3-diamine hydrochloride are applied to catalyze amide bond formation between terminal carboxyl group on sensor or nanoparticle surface and primary amine on polymerase or primer. Sensor or nanoparticle conjugated biopolymer may be immersed in solution containing Tris-HCl, pH 8.5 (25° C.), MgCl₂, primer or polymerase, dNTP and 110- or 536-bp dsDNA template. A system consisting of a sensor or nanoparticle conjugated biopolymer and solution containing buffered polymerase chain reaction components may be incubated at 60° C. Pulses from a Ti:sapphire laser system (tunable 600-3000 nm; 50-fs pulse duration; 50 uJ-pulse) are applied 1 kHz to raise system temperature 34° C. to 94° C. via thermal pulse dissipation to denature dsDNA template. Temperature may be maintained for 0.1 second. Pulses from Ti:sapphire laser system are applied at 1 kHz to raise system temperature 12° C. to 72° C. to extend dsDNA. Temperature may be maintained 0.2 seconds. Between Ti:sapphire laser pump pulses, surface-plasmon-resonance active surface may be interrogated by probe pulses at the resonant absorption frequency of gold particles or the dip angle for the surface-plasmon-resonance active surface to detect mass elongation and amplification of template at concentrations as low as 1-500 femtomolar. Temperature cycling may be repeated 25-30 times to amplify template. Fluorescence resonance enhanced transfer may be used to characterize interaction of conjugated biopolymer with template DNA and evaluate amplification efficiency.

LITERATURE CITED

The contents of the entirety of each of which are incorporated herein by this reference Asai, R.; Ootani, K.; Nomura, Y.; Nakamura, C.; Ikebukuro, K.; Arikawa, Y.; Miyake, J.; Karube, I. PCR-Based Ribosomal DNA Detection Technique for Microalga (Heterosigma carterae) Causing Red Tide and its Application to a Biosensor Using Labeled Probe. Marine Biotechnology (2003), 5(5), 417-423.

Boyer, D.; Tamarat, P.; Maali, A.; Lounis, B.; Orrit, M. *Photothermal imaging of nanometer-sized metal particles among scatterers. Science* (2002), 297, 1160-1163.

Caplin, B. E.; Rasmussen, R. P.; Bernard, P. S.; Wittwer, C. T. *The most direct way to monitor PCR amplification for quantification and mutation detection. Biochemica* (1999), 1, 5-8.

Carslaw H. S.; Jaeger, J. C. Conduction of Heat in Solids. $2^{nd}$ Ed. Clarendon Press: Oxford. 1959 Cooper, F. Int J Heat Mass Transfer (1977) 991.

Demers, L. M; Oestblom, M; Zhang, H.; Jang, N.-H.; Liedberg, B.; Mirkin, C. A. *Thermal Desorption Behavior and Binding Properties of DNA Bases and Nucleosides on Gold. Journal of the American Chemical Society* (2002), 124(38), 11248-11249.

Densham, D. H. *Polynucleotide sequencing method using an immobilized DNA polymerase. PCT Int. Appl.* (2002) Application: WO 2002-GB2345 20020520.

Duff, D. G.; Baiker, A.; Edwards, P. P. *A new hydrosol of gold clusters. 1. Formation and particle size variation. Langmuir* (1993), 9(9), 2301-9.

Feriotto, G.; Gambari, R. *Surface plasmon resonance based biosensor technology for real-time detection of PCR products. PCR Technology* (2nd Edition) (2004), 141-153.

Goodrich, T. T.; Lee, H. J.; Corn, R. M. Direct Detection of Genomic DNA by Enzymatically Amplified SPR Imaging Measurements of RNA Microarrays. Journal of the American Chemical Society (2004), 126(13), 4086-4087.

Halte, V.; Bigot, J.-Y.; Palpant, B.; Broyer, M.; Prevel, B.; Perez, A. Size dependence of the energy relaxation in silver nanoparticles embedded in dielectric matrices. Applied Physics Letters (1999), 75(24), 3799-3801.

Hamad-Schifferil, K.; Schwartz, J. J.; Santos, A. T.; Zhang, S.; Jacobson, J. M. Remote electronic control of DNA hybridization through inductive coupling to an attached metal nanocrystal antenna. Nature (London, United Kingdom) (2002), 415(6868), 152-155.

Hartland, Gregory V. Coherent vibrational motion in metal particles: Determination of the vibrational amplitude and excitation mechanism. Journal of Chemical Physics (2002), 116(18), 8048-8055.

He, L.; Musick, M. D.; Nicewamer, S. R.; Salinas, F. G.; Benkovic, S. J.; Natan, M. J.; Keating, C. D. Colloidal Au-enhanced surface plasmon resonance for ultrasensitive detection of DNA hybridization. Journal of the American Chemical Society (2000), 122(38), 9071-9077.

Hu, M.; Hartland, G. V. Heat Dissipation for Au Particles in Aqueous Solution: Relaxation Time versus Size. Journal of Physical Chemistry B (2002), 106(28), 7029-7033.

Hu, M.; Hartland, G. V. Heat Dissipation for Au Particles in Aqueous Solution: Relaxation Time versus Size [Erratum for 2002, Volume 106B]. Journal of Physical Chemistry B (2003), 107(5), 1284.

Hu, M.; Wang, X.; Hartland, G. V.; Salgueirino-Maceira, Veronica; Liz-Marzan, Luis M. Heat dissipation in gold-silica core-shell nanoparticles. Chemical Physics Letters (2003), 372(5,6), 767-772.

Huettmann, G.; Radt, B.; Serbin, J.; Birngruber, R. Inactivation of proteins by irradiation of gold nanoparticles with nano- and picosecond laser pulses. Proceedings of SPIE—The International Society for Optical Engineering (2003), 5142 (Therapeutic Laser Applications and Laser-Tissue Interactions), 88-95.

Hwang, H. J.; Kim, J. H. Method for Immobilizing DNA polymerase by covalent bonding for polymerase chain reaction. (S. Korea). U.S. Pat. Appl. Publ. (2004) 24 pp., Application: US 2003-406154 20030402.

Hwang, H. J.; Kim, J. H.; Jeong, K. Method and apparatus for amplification of nucleic acid sequences using polymerase chain reaction and immobilized DNA polymerase. PCT Int. Appl. (2003) 36 pp. Application: WO 2002-KR1900 20021011.

Hwang, H. J.; Kim, J. H.; Rhim, G. Immobilized DNA polymerase. PCT Int. Appl. (2002) 41 pp. Application: WO 2001-KR1650 20010929.

Iborra, F. J.; Pombo, A.; McManus, J.; Jackson, D. A.; Cook, P. R. The topology of transcription by immobilized polymerases. Experimental Cell Research (1996), 229(2), 167-173.

Incropera, F. P.; DeWitt, D. P. Fundamentals of Heat and Mass Transfer. $2^{nd}$ Ed. John Wiley & Sons: New York. 1985.

Jin R.; Wu G.; Li Z.; Mirkin C. A.; Schatz G. C. What Controls the Melting Properties of DNA-Linked Gold Nanoparticle Assemblies? J. Am. Chem. Soc. (2003) 125:1643-1654.

Kai, E.; Sawata, S.; Ikebukuro, K.; Iida, T.; Honda, T.; Karube, I. Detection of PCR products in solution using surface plasmon resonance. Analytical Chemistry (1999), 71(4), 796-800.

Kornberg, A.; Baker, T. A. DNA Replication $2^{nd}$ Ed. W.H. Freeman & Co: New York 1991.

Lindroos, K.; Liljedahl, U.; Raitio, M.; Syvanen, A.-C. Minisequencing on oligonucleotide microarrays: comparison of immobilization chemistries. Nucleic Acids Research (2001), 29(13), e69/1-e69/9.

Link, S.; El-Sayed, M. A. Optical properties and ultrafast dynamics of metallic nanocrystals. Annual Review of Physical Chemistry (2003), 54 331-366.

Molecular Biology of the Cell@NCBI, Accessed May, 2004. (http://www.ncbi.nlm.nih.gov/books/bv.fcgi?tool=bookshelf&call=bv.View.Show Section&searchterm=human&rid=cell.section.1607#1608)

Myszka, D. G.; He, X.; Dembo, M.; Morton, T. A.; Goldstein, B. Extending the range of rate constants available from BIACORE: interpreting mass transport-influenced binding data. Biophysical Journal (1998), 75(2), 583-594.

Nilsson, J.; Bosnes, M.; Larsen, F.; Nygren, P.-A.; Uhlen, M.; Lundeberg, J. Heat-mediated activation of affinity-immobilized Taq DNA polymerase. BioTechniques (1997), 22(4), 744-746, 748-751.

Oldenburg, S. J.; Jackson, J. B.; Westcott, S. L.; Halas, N. J. Infrared extinction properties of gold nanoshells. Applied Physics Letters (1999), 75(19), 2897-2899.

Park, S-J.; Taton, T. A.; Mirkin, C. A. Array-based electrical detection of DNA with nanoparticle probes. Science (2002), 295(5559), 1503-1506.

Pastinen, T.; Kurg, A.; Metspalu, A.; Peltonen, L.; Syvanen, A.-C. Minisequencing: a specific tool for DNA analysis and diagnostics on oligonucleotide arrays. Genome Research (1997), 7(6), 606-614.

Pelletier, J. Improving processivity of DNA- or RNA-dependent polymerases with nucleic acid-binding proteins and application to improved cDNA cloning. PCT Int. Appl. (2000) 43 pp. Priority: US 99-124011 19990312.

Power, G. M.; Barrett, D. A.; Davies, M. C.; Pitfield, I. D.; Shaw, P. N. The study of BSA adsorption onto model-reversed phase chromatography surfaces using surface plasmon resonance. Book of Abstracts, 216th ACS National Meeting, Boston, Aug. 23-27 (1998).

Radt, B.; Serbin, J.; Lange, B. I.; Birngruber, R.; Huettmann, G. Laser-generated micro- and nanoeffects: inactivation of proteins coupled to gold nanoparticles with nano- and picosecond pulses. Proceedings of SPIE—The International Society for Optical Engineering (2001), 4433(Laser-Tissue Interactions, Therapeutic Applications, and Photodynamic Therapy), 16-24.

Roper, D. K. Enhancing Lateral mass transport to Improve the Dynamic Range of Adsorption Rates Measured by Surface Plasmon Resonance. Chem. Eng. Sci. (2006), 61(8), 2557-2564.

Roper, D. K. 2004a. Direct Measurement of Sorption on Three-Dimensional Surfaces Such as Resins, Membranes or Other Preformed Materials Using Lateral Dispersion to Estimate Rapid Sorption Kinetics or High Binding Capacities. U.S. Patent Pending. United States Patent and Trademark Office assigned Application Ser. Nos. 60/626,566.

Roper, D. K. 2004b. Enhancing Lateral Mass Transport to Improve the Dynamic Range of Surface Plasmon Resonance and to Measure Macromolecule Adsorption Directly on 3-D Surfaces. Biophysical Journal. Submitted.

Roper, D. K. 2004c. Adenovirus Binding Measured by Surface Plasmon Resonance. AIChE Annual Meeting, Austin Tex. November 8-12.

Roper, D. K.; Johnson, A; Lee, A; Taylor, J; Trimor, C; Wen, E. Membrane Filtration in Vaccine Bioprocessing. First International Conference on Membrane and Filtration Technology in Biopurification, Cambridge, U.K. Apr. 7-9, 1999.

Roper, D. K.; Lightfoot, E. N. Estimating Plate Heights in Stacked-Membrane Chromatography by Flow-Reversal. J. Chromatogr. A. 702(1-2) (1995) 69-80.

Roper, D. K., Nakra, S. Adenovirus Type 5 Intrinsic Adsorption Rates Measured by Surface Plasmon Resonance. Anal. Biochem. (2006), 348, 75-83.

Roper, D. K.; Nakra, S. Surface Plasmon Resonance of Adenovirus Type 5 Binding to Diethylaminoethyl-Derivatized Self Assembled Monolayers. Analytical Chemistry. Submitted 2004.

Roper, D. K.; Purdom, G. Adenovirus Binding, Elution and Equilibrium Measured by Surface Plasmon Resonance. PREP 2004, Baltimore, Md. May 24-26, 2004.

Schultz, D. A. Plasmon Resonant Particles for Biological Detection. Curr Opin Biotechnol. 2003 14:13-22.

Storhoff, J. J.; Elghanian, R.; Mirkin, C. A.; Letsinger, R. L. Sequence-Dependent Stability of DNA-Modified Gold Nanoparticles. Langmuir (2002), 18(17), 6666-6670.

Svitel, J.; Balbo, A.; Mariuzza, R. A.; Gonzales, N. R.; Schuck, P. Combined affinity and rate constant distributions of ligand populations from experimental surface binding kinetics and equilibria. Biophysical Journal (2003), 84(6), 4062-4077.

Talmaci R; Traeger-Synodinos J; Kanavakis E; Coriu D; Colita D; Gavrila L. Scanning of beta-globin gene for identification of beta-thalassemia mutation in Romanian population. Journal of cellular and molecular medicine (2004 April-June), 8(2), 232-40.

Taton, T. A.; Mirkin, C. A.; Letsinger, R. L. 2000. Science 298:1757.

Tsoi, P. Y.; Yang, J.; Sun, Y.; Sui, S.; Yang, M. Surface Plasmon Resonance Study of DNA Polymerases Binding to Template/Primer DNA Duplexes Immobilized on Supported Lipid Monolayers. Langmuir (2000), 16(16), 6590-6596.

Vet, J. A. M.; Marras, S. A. E. Design and optimization of molecular beacon real-time polymerase chain reaction assays. Methods in Molecular Biology (Totowa, N.J., United States) (2005), 288(Oligonucleotide Synthesis), 273-290.

Wang, Y.; Prosen, D. E.; Mei, L.; Sullivan, J. C.; Finney, M.; Vander Horn, P. B. A novel strategy to engineer DNA polymerases for enhanced processivity and improved performance in vitro. Nucleic Acids Research (2004), 32(3), 1197-1207.

Westcott, S. L.; Averitt, R. D.; Wolfgang, J. A.; Nordlander, P.; Halas, N. J. Adsorbate-Induced Quenching of Hot Electrons in Gold Core-Shell Nanoparticles. Journal of Physical Chemistry B (2001), 105(41), 9913-9917.

Wilson, O. M.; Hu, X.; Cahill, D. G.; Braun, P. V. Colloidal metal particles as probes of nanoscale thermal transport in fluids. Physical Review B: Condensed Matter and Materials Physics (2002), 66(22), 224301/1-224301/6.

Wittwer, C. T.; Herrmann, M. G.; Moss, A. A.; Rasmussen, R. P. Continuous fluorescence monitoring of rapid cycle DNA amplification. BioTechniques (1997), 22(1), 130-131, 134-138.

What is claimed is:

1. A method of performing a Polymerase-Chain-Reaction (PCR) using surface plasmon resonance (SPR), the method comprising:
   providing a PCR reaction cell that includes a surface plasmon active surface;
   contacting the surface plasmon active surface with an aqueous medium comprising or in fluid contact with a template, a primer capable of annealing to the template, dNTPs, and a thermostable polymerase, wherein the aqueous medium, the template, the primer, the dNTPs, and the thermostable polymerase are substantially free of dyes or labels;
   performing an SPR-induced PCR amplification with the template, the primer, the dNTPs, and the thermostable polymerase, wherein the SPR-induced PCR amplification includes:
   allowing the primer to anneal to the template;
   heating a portion of the aqueous medium that is in contact with the surface plasmon active surface by exciting surface plasmons at an interface between the surface plasmon active surface and the aqueous medium so as to induce selective decay of the excited surface plasmons such that decaying surface plasmons heat the aqueous medium adjacent to the surface plasmon active surface to a temperature selected to allow elongation of the primer;
   elongating the primer using the thermostable polymerase at the temperature selected to allow elongation of the primer; and
   heating a portion of the aqueous medium that is in contact with the surface plasmon active surface by exciting surface plasmons at the interface between the surface plasmon active surface and the aqueous medium so as to induce selective decay of the excited surface plasmons such that decaying surface plasmons heat the aqueous medium adjacent to the surface plasmon active surface to a temperature selected to denature the elongated primer and the template.

2. The method of claim 1, wherein the surface plasmon active surface comprises a surface of a nanoparticle.

3. The method of claim 2, wherein the nanoparticle is selected from the group consisting of surface plasmon active nanoparticles, nanoshells, and nanocylinders.

4. The method according to claim 1, further comprising immobilizing at least one of the template, the primer capable of annealing to the template, and the thermostable polymerase on the surface plasmon active surface.

5. The method according to claim 4, wherein immobilizing at least one of the template, the primer capable of annealing to the template, and the thermostable polymerase on the surface plasmon active surface comprises using N-hydroxysuccinimide.

6. The method according to claim 1, wherein the Polymerase-Chain-Reaction is a multiplex Polymerase-Chain-Reaction.

7. The method according to claim 1, wherein heating the portion of the aqueous medium that is in contact with the surface plasmon active surface to a temperature selected to allow elongation of the primer is performed on a millisecond time scale.

8. The method according to claim 1, wherein heating the portion of the aqueous medium that is in contact with the surface plasmon active surface to a temperature selected to allow denaturation of the elongated primer and the template is performed on a millisecond time scale.

9. The method according to claim 1, further comprising detecting mass elongating of the primer and amplification of the template using surface plasmon resonance.

10. The method according to claim 1, wherein the optical source is capable of emitting light with a wavelength of about 500 nm to about 900 nm.

11. The method according to claim 1, wherein the optical source is selected from the group consisting of a laser, Ti:sapphire laser, an argon-ion laser, a krypton laser, a xenon lamp, and an light-emitting diode.

12. A method of real time detection of Polymerase-Chain-Reaction (PCR) amplicons by Surface-Plasmon-Resonance (SPR), said method comprising:

immobilizing a polymerase or a polynucleotide primer on a surface plasmon active surface;

providing, in fluid contact with the surface plasmon active surface, a PCR reaction mix that comprises a PCR template, dNTPs, and a polymerase or a polynucleotide primer if not already immobilized on the surface plasmon active surface, wherein the PCR reaction mix is substantially free of dyes or labels;

cycling an annealing temperature, an elongation temperature, and a denaturation temperature of an area within about 189 nm adjacent to the surface plasmon active surface using a first SPR excitation technique so as to perform PCR using the polymerase, primer, PCR template, and dNTPs;

wherein cycling the temperature of an area adjacent the surface plasmon active surface so as to perform PCR comprises heating the area adjacent the surface plasmon active surface by exciting surface plasmons at an interface between the surface plasmon active surface and the aqueous medium so as to induce selective decay of the excited surface plasmons such that decaying surface plasmons heat the aqueous medium adjacent to the surface plasmon active surface; and measuring rates and magnitudes of interaction between the template and molecules immobilized on the surface plasmon active surface using a second SPR excitation technique that is different than the first SPR excitation technique for analyzing mass-induced changes in resonance absorption, wherein the second SPR excitation technique does not induce heating of the area adjacent the surface plasmon active surface.

13. The method according to claim 12, wherein cycling between the annealing temperature and the elongation temperature occurs on a millisecond time scale.

14. The method according to claim 12, wherein cycling between the elongation temperature and the denaturation temperature occurs on a millisecond time scale.

15. The method according to claim 12 wherein the optical source stimulates surface plasmon resonance.

16. The method according to claim 15, wherein the optical source is capable of emitting light with a wavelength of about 500 nm to about 900 nm.

17. The method according to claim 15, wherein the optical source is selected from the group consisting of a laser, Ti:sapphire laser, an argon-ion laser, a krypton laser, a xenon lamp, and an light-emitting diode.

18. The method according to claim 12, wherein the surface plasmon active surface comprises a nanoparticle.

19. The method of claim 1, wherein heating portion of the aqueous medium that is in contact with the surface plasmon active surface to allow elongation and denaturation is accomplished without inducing direct bulk heating of the aqueous medium.

20. The method of claim 1, wherein heating portion of the aqueous medium that is in contact with the surface plasmon active surface comprises directly heating an area within about 44 to about 189 nm adjacent to the surface plasmon active surface.

21. The method of claim 1, wherein heating portion of the aqueous medium that is in contact with the surface plasmon active surface comprises directly heating an area within about 189 nm adjacent to the surface plasmon active surface.

22. The method claim 12, wherein the surface plasmon active surface is a gold surface.

* * * * *